US009937267B2

(12) United States Patent
Falconer et al.

(10) Patent No.: US 9,937,267 B2
(45) **Date of Patent: *Apr. 10, 2018**

(54) METHODS OF TREATING CANCER USING COMPOUNDS CONTAINING A VASCULAR DISRUPTING AGENT

(71) Applicant: Incanthera Ltd, Bradford (GB)

(72) Inventors: Robert Andrew Falconer, West Yorkshire (GB); Jason Gill, Leeds (GB); Jennifer Xavier, Needingworth (GB); Paul Loadman, Bradford (GB); Michael Bibby, Bingley (GB); Laurence Patterson, West Yorkshire (GB)

(73) Assignee: Incanthera Ltd, Manchester (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/297,649

(22) Filed: Oct. 19, 2016

(65) Prior Publication Data

US 2017/0266307 A1 Sep. 21, 2017

Related U.S. Application Data

(63) Continuation of application No. 14/553,803, filed on Nov. 25, 2014, now abandoned, which is a continuation of application No. 13/125,732, filed as application No. PCT/GB2009/002484 on Oct. 20, 2009, now Pat. No. 8,927,486.

(30) Foreign Application Priority Data

Oct. 22, 2008 (GB) .................................. 0819287.4

(51) Int. Cl.

| | |
|---|---|
| ***A61K 47/48*** | (2006.01) |
| ***C07K 7/06*** | (2006.01) |
| ***A61K 38/08*** | (2006.01) |
| ***A61P 35/00*** | (2006.01) |
| ***A61K 31/165*** | (2006.01) |
| ***A61K 31/135*** | (2006.01) |

(52) U.S. Cl.

CPC ...... *A61K 47/48338* (2013.01); *A61K 31/135* (2013.01); *A61K 31/165* (2013.01); *A61K 47/481* (2013.01); *A61K 47/48215* (2013.01); *C07K 7/06* (2013.01)

(58) Field of Classification Search

CPC ............ A61K 47/481; A61K 47/48215; A61K 47/48338; A61K 31/135; A61K 31/165; C07K 7/06

See application file for complete search history.

(56) References Cited

U.S. PATENT DOCUMENTS

| | | | |
|---|---|---|---|
| 5,595,756 A | 1/1997 | Bally et al. | |
| 8,927,486 B2 | 1/2015 | Falconer et al. | |
| 2003/0195152 A1 | 10/2003 | Suarato et al. | |
| 2006/0074008 A1 | 4/2006 | Senter et al. | |
| 2007/0117133 A1 | 5/2007 | Trieu et al. | |
| 2010/0168036 A1 | 7/2010 | Gill et al. | |

FOREIGN PATENT DOCUMENTS

| | | |
|---|---|---|
| EP | 1862470 A1 | 12/2007 |
| WO | WO-01/068145 | 9/2001 |
| WO | WO-02/072620 | 9/2002 |
| WO | WO-05/023314 | 3/2005 |
| WO | WO-06/079120 A2 | 7/2006 |
| WO | WO-06/090813 A1 | 8/2006 |
| WO | WO-06/110476 | 10/2006 |
| WO | WO-08/125800 | 10/2008 |

OTHER PUBLICATIONS

"Matrix Metalloproteinases." *MM P.* (2007):1-15.
Aitkhozhina et al. "10-Amino Analogs of Colchicine: Synthesis, Structure, and Biological Activity." *Bioorganicheskaia Khimia.* 22.5:383-386. (Russian Original and English Abstract), Abstract only, 1996.
Albright, Charles F., et al., "Matrix-Metalloproteinase-Activated Doxorubicin Prodrugs Inhibit HT1080 Zenograft Growth Better than Doxorubicin with Less Toxicity," Molecular Cancer Therapeutics, v. 4, No. 5, p. 751-760, May 1, 2005.
Atkinson et al, Development of a Novel Tumor-Targeted Vascular Disrupting Agent Activated by Membrane-Type Matrix Metalloproteinases, Cancer Res, 2010, 70, pp. 6902-6912.
Auerbach et al, Angiogenesis assays: Problems and pitfalls, Cancer and Metastasis Reviews, 2000, 19, pp. 167-172.
Bradley et al., Limits of Cooperativity in a Structurally Modular Protein: Response of the Notch Ankyrin Domain to Analogous Alanine Substitutions in Each Repeat, J. Mol. BIoL (2002) 324, 373-386.
Beerepoot et al. "Phase I Clinical Evaluation of Weekly Administration of the Novel Vascular-Targeting Agent, ZD6126, in Patients with Solid Tumors." *J. Clin. Oncol.* 24.10(2006):14911498.
Berendsen, A Glimpae of the Holy Grail? Science, 1998, 282, pp. 642-643.
Cancer Drug Design and Discovery. Neidle, Stephen, ed., Elsevier/ACademic Press, 2008, p. 427-431.
Cellular and Molecular Basis of Cancer-Merck Manual, from http://www.merckmanuals.com/professional/print/hematology_and_oncology/overview_of . . . , pp. 1-5, accessed Nov. 7, 2012.
Chau, Ying, et al., "Synthesis and Characterization of Dextran-Peptide-Methotrexate Conjugates for Tumor Targeting via Mediation by Matrix metalloproteinase II and Matrix Metalloproteinase IX," Bioconjugate Chemistry, v. 15, No. 4, p. 931-941, Jul. 1, 2004.
Chaudhuri et al. "The Interaction of the B-ring of Colchicine with a-Tubulin: A Novel Footprinting Approach." *J. Mol. Biol.* 303. 5(2000):679-692.

(Continued)

*Primary Examiner* — Julie Ha
*Assistant Examiner* — Li N Komatsu
(74) *Attorney, Agent, or Firm* — Mintz Levin Cohn Ferris Glovsky and Popeo, P.C.; Muriel Liberto, Esq.

(57) ABSTRACT

The present invention relates to prodrugs of vascular disrupting agents comprising a vascular disrupting agent (VDA) associated with a MMP proteolytic cleavage site and to the use of such prodrugs in the targeted treatment of cancer.

28 Claims, 10 Drawing Sheets

(56) References Cited

OTHER PUBLICATIONS

Daoud et al, Reduced Toxicity and Enhanced Antitumor Effects in Mice of the Ionophoric Drug Valinomycin When Incorporated in Liposomes, Cancer Res, 1986, 46 pp. 5518-5523.
Davis, Peter D., et al., "ZD6126: A Novel Vascular-Targeting Agent that Causes Selective Destruction of Tumor Vasculature," Cancer Research, v. 62, No. 24, p. 7247-7253, Dec. 15, 2002.
Definition of derivative and analog, from http://cancerweb.ncl.ac.uk/omd/about.html, pp. 15, accessed Jul. 7, 2005.
Denekamp. "Endothelial Cell Proliferation as a Novel Approach to Targeting Tumour Therapy." *Br. J. Cancer*. 45(1982):136-139.
Dubowchik, Gene M., et al., "Receptor-Mediated and Enzyme-Dependent Targeting of Cytotoxic Anticancer Drugs," Pharmacology and Therapeutics, v. 83, p. 67-123, Jan. 1, 1999.
Egeblad et al, New Functions for the Matrix Metalloproteinases in Cancer Progression, Nature Reviews Cancer, 2002, 2, pp. 161-174.
Esbolaev et al. "C-10 Amino Acid Derivatives of Colchicine." *Chem. Nat. Compounds*. 28.34(1992):325-328.
Esbolaev et al. "C-10 Dipeptide Derivatives of Colchicine." *Khimiya Prirodnykh Soedinenii*. 1(1989):91-95. (Russian Original English Abstract), Abstract only.
Esbolaev et al. "Cytotoxic Activity of Dipeptide Derivatives of Colchicine." *Izvestiya Akademii Nauk Kazakhskoi SSR*. 5(1989):83-86. (Russian Original and English Abstract), Abstract only.
Gill, J.H. et al. (Apr. 7, 2014, e-published Mar. 27, 2014). "Tumor-targeted prodrug ICT2588 demonstrates therapeutic activity against solid tumors and reduced potential for cardiovascular toxicity," *Molecular Pharmaceutics* 11(4):1294-1300.
Gura, Systems for Identifying New Drugs Are Often Faulty, Science, 1997, 278, pp. 1041-1042.
Hamel. "Antimitotic Natural Products and Their Interactions with Tubulin." *Med. Res. Rev*. 16.2(1996):207-231.
Hollebecque et al, Vascular disrupting agents: a delicate balance between efficacy and side effects, Current Opinion Oncology, 2012, 24, pp. 305-315.
Hooper et al, Chapter 2 Identification and Development of Vascular Disrupting Agents: Natural Products That Interfere with Tumor Growth, from Natural Products and Cancer Drug Discovery, Ed. F.E, Koehn, 2013, pp. 17-39.
Itoh, Membrane-type matrix metalloproteinases: Their functions and regulations, Matrix Biol., 2015, 44-46, pp. 207-223.
Jain, Barriers to Drug Delivery in Solid Tumors, Scientific American, 1994, pp. 58-65.
Kline, Toni, et al., "Novel Antitumor Prodrugs Designed for Activation by Matrix Metalloproteinases-2 and -9" Molecular Pharmaceutics, v. 1, No. 1, p. 9-22, Jan. 12, 2004.
Kratz, Felix, et al., "Development and in Vitro Efficacy of Novel MMP2 and MMP9 Specific Doxorubicin Albumin Conjugates," Bioorganic & Medicinal Chemistry Letters, v. 11, No. 15, p. 2001-2006, Aug. 6, 2001.
Kratz, Felix, et al., "Prodrugs of Anthracyclines in Cancer Chemotherapy" Current Medicinal Chemistry, v. 13, No. 5, p. 477-523, Jan. 1, 2006.
Lippert. "Vascular Disrupting Agents." *Bioorg. Med. Chem.* 15.2(2007):605-615.
Mansour, Ahmed M., et al., "A New Approach for the Treatment of Malignant Melanoma: Enhanced Antitumor Efficacy of an Albumin-Binding Doxorubicin Prodrug that is Cleaved by Matrix Metalloproteinase 2," Cancer Research, v. 63, No. 14, p. 4062-4066, Jul. 15, 2003.
Nagase et al. "Human Matrix Metalloproteinase Specificity Studies using Collagen Sequence-Based Synthetic Peptides." *Biopolymers*. 40(1996):399-416.
Ngo et al, Computational Complexity, Protein Structure Protection, and the Levinthal Paradox, 1994, pp. 491-494.
Quinn et al. "Toxicity Quantitative Structure—Activity Relationships of Colchicines." *J. Med. Chem*. 24.5(1981):636-639.
*Remington's Pharmaceutical Sciences*. Gennaro, ed. Easton, PA: Mack Publishing Co. (1985):1418.
Rudinger, Peptide Hormones, JA Parsons, Ed., 1976, pp. 1-7.
Rustin et al. "Phase I Clinical Trial of Weekly Combretastatin A4 Phosphate: Clinical and Pharmacokinetic Results." *J. Clin. Oncol*. 21.15(2003):2815-2822.
Siemann et al. "Differentiation and Definition of Vascular-Targeted Therapies." *Clin. Cancer Res*. 11(2005):416-420.
SIGMA, 2004, pp. 1-2.
Sporn et al, Chemoprevention of cancer, Carcinogenesis, 2000, 21, pp. 525-530.
Tozer et al. "Disrupting Tumour Blood Vessels." *Nat. Rev. Cancer*. 5.6(2005):423-435.
Voet et al, Biochemistry, John Wiley & Sons Inc., 1995, pp. 235-241.

SEQUENCE LISTING

```
<160> NUMBER OF SEQ ID NOS: 4

<210> SEQ ID NO 1
<211> LENGTH: 7
<212> TYPE: PRT
<213> ORGANISM: Artificial Sequence
<220> FEATURE:
<223> OTHER INFORMATION: sequence motif for MMP proteolytic cleavage
      site
<220> FEATURE:
<221> NAME/KEY: MOD_RES
<222> LOCATION: (3)...(3)
<223> OTHER INFORMATION: 2-Amino-4-phenylbutyric acid =
      homophenylalanine
<220> FEATURE:
<221> NAME/KEY: MOD_RES
<222> LOCATION: (5)...(5)
<223> OTHER INFORMATION: 2-Amino-5-ureidopentanoic acid = citrulline

<400> SEQUENCE: 1

Leu Tyr Phe Gly Arg Ser Arg
1               5


<210> SEQ ID NO 2
<211> LENGTH: 9
<212> TYPE: PRT
<213> ORGANISM: Artificial Sequence
<220> FEATURE:
<223> OTHER INFORMATION: sequence motif for MMP proteolytic cleavage
      site
<220> FEATURE:
<221> NAME/KEY: MOD_RES
<222> LOCATION: (1)...(1)
<223> OTHER INFORMATION: bAla
<220> FEATURE:
<221> NAME/KEY: MOD_RES
<222> LOCATION: (4)...(4)
<223> OTHER INFORMATION: 2-Amino-5-ureidopentanoic acid = citrulline
<220> FEATURE:
<221> NAME/KEY: MOD_RES
<222> LOCATION: (6)...(6)
<223> OTHER INFORMATION: 2-Amino-4-phenylbutyric acid =
      homophenylalanine

<400> SEQUENCE: 2

Ala Glu Pro Arg Gly Phe Tyr Leu Tyr
1               5


<210> SEQ ID NO 3
<211> LENGTH: 9
<212> TYPE: PRT
<213> ORGANISM: Artificial Sequence
<220> FEATURE:
<223> OTHER INFORMATION: sequence motif for MMP proteolytic cleavage
      site
<220> FEATURE:
<221> NAME/KEY: MOD_RES
<222> LOCATION: (1)...(1)
<223> OTHER INFORMATION: bAla
<220> FEATURE:
<221> NAME/KEY: MOD_RES
<222> LOCATION: (4)...(4)
```

-continued

```
<223> OTHER INFORMATION: 2-Amino-5-ureidopentanoic acid = citrulline
<220> FEATURE:
<221> NAME/KEY: MOD_RES
<222> LOCATION: (6)...(6)
<223> OTHER INFORMATION: 2-Amino-4-phenylbutyric acid =
      homophenylalanine

<400> SEQUENCE: 3

Ala Arg Ser Arg Gly Phe Tyr Leu Tyr
1               5


<210> SEQ ID NO 4
<211> LENGTH: 8
<212> TYPE: PRT
<213> ORGANISM: Artificial Sequence
<220> FEATURE:
<223> OTHER INFORMATION: sequence motif for MMP proteolytic cleavage
      site
<220> FEATURE:
<221> NAME/KEY: MOD_RES
<222> LOCATION: (3)...(3)
<223> OTHER INFORMATION: 2-Amino-5-ureidopentanoic acid = citrulline
<220> FEATURE:
<221> NAME/KEY: MOD_RES
<222> LOCATION: (5)...(5)
<223> OTHER INFORMATION: 2-Amino-4-phenylbutyric acid =
      homophenylalanine

<400> SEQUENCE: 4

Arg Ser Arg Gly Phe Tyr Leu Tyr
1               5
```

METHODS OF TREATING CANCER USING COMPOUNDS CONTAINING A VASCULAR DISRUPTING AGENT

CROSS-REFERENCE TO RELATED APPLICATIONS

This application is a continuation of U.S. Ser. No. 14/553,803 filed on Nov. 25, 2014, now abandoned, which is a continuation of U.S. Ser. No. 13/125,732 filed on Jul. 12, 2011, now U.S. Pat. No. 8,927,486, which is a US National Phase Application of PCT Patent Application No. PCT/GB2009/002484, filed Oct. 20, 2009, which claims priority to GB Patent Application No. 0819287.4, filed Oct. 22, 2008, which are incorporated herein by reference in their entireties.

FIELD OF THE INVENTION

The present invention relates to prodrugs of vascular disrupting agents and to the use of such compounds in the targeted treatment of cancer.

INCORPORATION BY REFERENCE OF SEQUENCE LISTING

The contents of the computer readable form of the Sequence Listing filed in the application and 3 KB in size, is hereby incorporated by reference in its entirety.

BACKGROUND TO THE INVENTION

Targeting tumour vasculature as a molecular approach to cancer chemotherapies is becoming one of the highest scientific priorities. Two drug models are emerging, i.e. one that prevents the formation of new blood vessels in the tumour (antiangiogenesis) and one that targets vascular destruction.

Disruption of even a small proportion of the tumour vasculature has been demonstrated to induce wide ranging tumour death and retardation of metastasis, since a single blood vessel is responsible for supporting the survival of many tumour cells. Endothelial cells, which form the major component of the vasculature, are highly dependent upon the tubulin cytoskeleton for their motility, invasion, attachment, alignment and proliferation (Denekamp, J, Br J Cancer, 45, 136-139 (1982)). Agents which disrupt the endothelial microtubule network will therefore cause a rapid collapse in tumour blood flow and a prolonged period of vascular shutdown, culminating in extensive tumour-cell necrosis (Tozer et al., Nat Rev Cancer, 5, 423-435 (2005), Lippert J W, Bioorg Med Chem, 15, 605-615 (2007)).

One of the most potent classes of cancer therapeutic drugs are the vascular disrupting agents (VDAs) which characteristically have good in vitro cell cytotoxicities but often show poor specificity for killing tumour over normal tissues in vivo. Furthermore, many VDAs such as the tubulin binding agents are water insoluble and require formulation before evaluation in the clinic. The present invention aims to address the aforementioned problems.

Colchicine and its analogues are potent VDAs causing haemorrhage and subsequent extensive necrosis in tumours (Tozer et al., Nat Rev Cancer, 5, 423-435 (2005)), as a direct consequence of tubulin binding and induction of microtubule depolymerisation (Chaudri et al., J Mol Biol, 303, 679-692 (2000)). Colchicine has not, however, shown intrinsic value as a clinically applicable anticancer therapeutic due to a high level of toxicity and consequent very narrow therapeutic index (Tozer et al., Nat Rev Cancer, 5, 423-435 (2005); Quinn et al., J Med Chem, 24, 636-639 (1981)). It would be desirable, therefore, to be able to target a VDA such as colchicine selectively to a tumour.

The present inventors have developed a system for overcoming the toxic effect of systemic administration of potent anti-cancer agents in particular vascular disrupting agents.

SUMMARY OF THE INVENTION

The present invention relates to prodrugs of vascular disrupting agents comprising a vascular disrupting agent (VDA) associated with a MMP proteolytic cleavage site and to the use of such prodrugs in the targeted treatment of cancer.

BRIEF DESCRIPTION OF THE DRAWINGS

The invention will now be described by way of example only with reference to the following Figures in which.

DETAILED DESCRIPTION OF THE INVENTION

Figure 1:
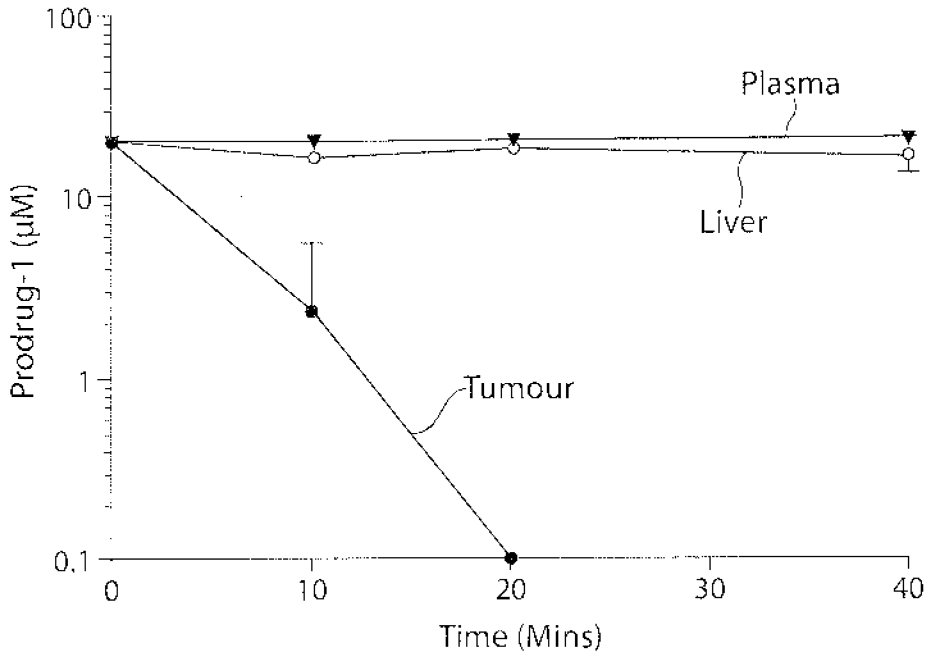
FIG. 1 is a graph showing the metabolism of prodrug-1 versus time in tumour and non-tumour tissues ex vivo.

The present invention is based, at least in part, on the selection of a proteolytic cleavage site which allows for the selective release of a vascular disrupting agent, such as colchicine, at the tumour vasculature.

According to a first aspect of the invention there is provided a compound, or pharmaceutically acceptable salt thereof, comprising a vascular disrupting agent (VDA) associated with a MMP proteolytic cleavage site. The term "associated with" in the context of the invention is intended to include all direct and indirect means of association, generally covalent, including, but not limited to, chemical cross-linking or peptide bond linkage.

Compounds of the invention may be in the form of salts. In particular, the salts may be pharmaceutically acceptable salts. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred, Lists of suitable salts are found in *Remington's Pharmaceutical Sciences,* 17th ed., Mack Publishing Company, Easton, Pa., US, 1985, p. 1418, the disclosure of which is hereby incorporated by reference; see also Stahl et al, Eds, "*Handbook of Pharmaceutical Salts Properties Selection and Use*", Verlag Helvetica Chimica Acta and Wiley-VCH, 2002.

The disclosure thus includes pharmaceutically-acceptable salts of the disclosed compounds wherein the parent compound is modified by making acid or base salts thereof. For example the conventional non-toxic salts or the quaternary ammonium salts which are formed, e.g. from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

In a preferred aspect the invention provides a compound of formula (I)

$$X—Y \qquad (I)$$

wherein

X is a vascular disrupting agent (VDA);

Y is a matrix metalloproteinase (MMP) proteolytic cleavage site.

Compounds according to the invention provide prodrugs which are converted to an, active and potent VDA within the tumour environment by overexpressed MMPs. Tumour selective activation of a prodrug of the invention increases tumour levels, and decreases systemic levels, of the VDA and optionally additional active ingredients thereby greatly increasing their therapeutic index and efficacy.

VDAs comprise a multi-ring system, for example a fused or unfused bicyclic or tricyclic ring system. Thus X includes any multi-ring system of a VDA that is capable of binding to and disrupting tumour blood vessels.

VDAs can be divided into three classes:

(i) those compounds that interact with tubulin at the colchicine binding site on tubulin;

(ii) those compounds that share a common binding site on tubulin with the Catharanthus (Vinca) alkaloids;

(iii) compounds that promote the formation of stable microtubules in a manner similar to paclitaxel, a novel taxane diterpenoid isolated from the bark of the Pacific yew.

In a preferred aspect of the invention the VDA is a tubulin binding agent. The tubulin binding agent may be selected from the group consisting of i) those which interact with tubulin at the colchicine binding site: including but not limited to colchicine (including colchicine analogues such as N-acetylcolchinol-O-phosphate (ZD6126) and ABT-751), colchicinoids, combretastatins phenstatin, podophyllotoxins, steganacins, amphethinile and stilbenes; and ii) those which interact with the Vinoa binding site of tubulin: including but not limited to vincristine, vinblastine, vinflunine, maytansinoids, phomopson A, rhizoxin, auristatin (including analogues thereof) and dolastatin.

In a preferred aspect of the invention the VDA is a tubulin binding agent that interacts with the colchicine binding site within tubulin. In one embodiment of the invention the VDA is colchicine or an analogue/derivative thereof. Colchicine analogues or derivatives may include, but are not limited to, azademethylcolchicine, azacolchicine, N-methyl desacetylcolchicine, desacetylcolchicine.

In an embodiment of the invention the VDA is a non-peptide VDA. For example a VDA according to the invention may be a tubulin binding agent that is not auristatin or a derivative thereof.

Alternatively the VDA may be a tubulin binding agent selected from the group consisting of, but not limited to, combretastatins (e.g. combretastatin A-4 3-O-phosphate), auristatin (including analogues thereof), dolastatin; and flavenoids (e.g. tumour necrosis factor a and 5,6-dimethylxanthenone-4-acetic acid (DMXAA), flavone acetic acid (FAA)). Thus in an alternative embodiment of the invention the VDA is a combretastatin.

The invention includes any member of the MMP family. Proteolytic cleavage at the MMP cleavage site by an MMP releases the VDA, and any other active agent associated with the MMP cleavage site, in active form.

The MMP family is divided into eight structural groups: five of which are secreted MMPs and three of which are membrane-type MMPs (MT-MMPs). MT-MMPs are localised on the cell surface. The invention includes secreted MMPs and membrane type MMPs.

In a preferred aspect of the invention the MMP is a membrane-type (MT-MMP). Thus the invention provides a compound of formula I wherein Y comprises a peptide sequence that is selectively cleaved by a MT-MMP. The MT-MMP may be selected from the group consisting of (i) type I transmembrane type MT-MMPs for example MMP-14 (MT1-MMP), MMP-15 (MT2-MMP), MMP-16 (MT3-MMP) and MMP-24 (MT5-MMP);

(ii) glycosyl phosphatidylinositol (GPI)-anchored structural group of MT-MMPs for example MMP-17 (MT4-MMP) and MMP-25 (MT6-MMP);

(iii) type II transmembrane class for example MMP-23.

The MMP cleavage site may comprise any peptide sequence having an amide bond, typically a peptide bond, which is cleavable by a MMP. Preferably Y is a peptide sequence comprising between two and twenty amino acids, for example between six and ten amino acids (e.g. 6, 7 or 8 amino acids). The amino acids may be D-amino acids or L-amino acids.

The MMP proteolytic cleavage site may comprise the sequence:

(i) P3'-P2'-P1'-P1-P2-P3 wherein P1' to P3' and P1 to P3, which may be the same or different, are amino acid residues and wherein proteolytic cleavage takes place across the bond between residues P1' and P1. Preferably MMP proteolytic cleavage site is MT-MMP specific cleavage site such that cleavage between P1 and P1' selectively takes place by a MT-MMP for example MT-MMP14.

The MMP proteolytic cleavage site may comprise the sequence:

(ii) P3'-P2'-P1'-P1-P2-P3-P4 wherein P1' to P3' and P1 to P4, which may be the same or different, are amino acid residues and wherein proteolytic cleavage takes place between residues P1' and P1.

The MMP proteolytic cleavage site may comprise the sequence:

(iii) P4'-P3'-P2'-P1'-P1-P2-P3-P4 wherein P1' to P4' and P1 to P4, which may be the same or different, are amino acid residues and wherein proteolytic cleavage takes place between residues P1' and P1.

In a preferred aspect of the invention P1 and P1' are different.

Preferably the MMP cleavage site comprises a peptide sequence which is selectively cleaved by a MT-MMP. Thus, in a preferred aspect the invention provides a compound of formula (I) wherein Y comprises the sequence (i), (ii) or (iii) in which P1' is a hydrophobic amino acid. As used herein, the terms "hydrophobic" may refer to amino acids having a hydrophobicity that is greater than or equal to −1.10 and/or a net charge that is greater than or equal to 0 as described in Fauchere and Pliska Eur. J. Med Chem. 10:39 (1983). A hydrophobic or non-polar amino acid may also refer to an amino acid having a side chain that is uncharged at physiological pH, is not polar and that is generally repelled by aqueous solution. A hydrophobic amino acid may be selected from the group consisting of leucine, phenylalanine, proline, alanine, tryptophan, valine, isoleucine, methionine, tyrosine and threonine. P1' may be an amino acid with an aliphatic side chain. Alternatively P1' may be an amino acid with an aromatic side chain. P1' may also include non-natural hydrophobic amino acids for example homophenylalanine (Hof).

A preferred aspect of the invention provides a compound of formula (I) wherein Y comprises the sequence (i), (ii) or (iii) in which P1 is a polar amino acid for example an amino acid selected from the group consisting of Asparagine (N), Serine (S) or Glycine (G). To improve selectivity for a MT-MMP at the cleavage site, it is preferred that P1 is not proline. Thus in an embodiment of the invention P1 is an amino acid excluding proline. In a further embodiment of the invention, P1 is glycine.

A preferred aspect of the invention provides a compound of formula (I) wherein Y comprises the sequence (i), (ii) or (iii) in which P2' is selected from the group consisting of polar, uncharged amino acids and/or basic amino acids including for example Arginine (R), Alanine (A), Leucine (L), Aspartic Acid (D), Tyrosine (Y), Threonine (T), Serine (S) and Proline (P). To improve selectivity for a MT-MMP at the cleavage site, P2' may be a methylated amino acid for example N-methyl tyrosine. The present inventors have found that cleavage by non MT-MMPs, for example MMP2, takes place at both the P1'-P2' and P2'-P3' sites when P2' is tyrosine. Thus in an embodiment of the invention P2' is not tyrosine.

As used herein, the P3' residue may comprise any amino acid. In one embodiment of the invention P3' is Leucine (L). Where present, the P4' residue may comprise an amino acid with a nucleophilic side chain for example Lysine (L), Cysteine (C), Serine (S), Tyrosine (Y), Threonine (T), Glutamic acid (E), or Aspartic acid (D).

A preferred aspect of the invention provides a compound of formula (I) wherein Y comprises the sequence (i), (ii) or (iii) in which P2 is selected from the group consisting of acidic (for example glutamic acid), basic, hydrophobic or polar amino acids. P2 may also include non-natural hydrophobic amino acids for example citrulline (Cit). To improve selectivity for a MT-MMP at the cleavage site, it is preferred that P2 is not proline. Thus in an embodiment of the invention P2 is an amino acid excluding proline.

A preferred aspect of the invention provides a compound of formula (I) wherein Y comprises the sequence (i), (ii) or (iii) in which P3 is a polar amino acid for example selected from the group consisting of Glycine (G), Alanine (A), Serine (S), Leucine (L), Isoleucine (I) and Threonine (T). It is preferred that P3 is not proline. Thus in an embodiment of the invention P3 is not proline. In a further embodiment of the invention P3 is serine.

A preferred aspect of the invention provides a compound of formula (I) wherein Y comprises the sequence (ii) or (iii) in which P4 is an amino acid containing a substantial side chain, for example an amino acid having a basic group in its side chain, including amino acids selected from the group consisting of Arginine (R) and Lysine (K). To improve selectivity for a MT-MMP at the cleavage site, it is preferred that P4 is arginine. Thus in an embodiment of the invention P4 is arginine.

A preferred aspect of the invention provides a compound of formula (I) wherein Y comprises the sequence (i), (ii) or (iii) wherein none of the residues are proline and wherein P4 is arginine.

Each of residues P1 to P3 or P4 may be different. Alternatively or additionally each of residues P1' to P3' or P4' is different.

One embodiment of the invention provides a compound of formula (I) wherein Y comprises the sequence (i), (ii) or (iii) in which P1 and/or P2 and/or P3 are an amino acid reside other than proline. Furthermore, in this embodiment P4 is arginine.

In a further embodiment of the invention there is provided a compound of formula (I) wherein Y comprises the sequence (i), (ii) or (iii) in which P1' is a hydrophobic amino acid and in which P1 and/or P2 and/or P3 are an amino acid reside other than proline.

In a yet further embodiment of the invention there is provided a compound of formula (I) wherein Y comprises the sequence (ii) or (iii) in which P1' is a hydrophobic amino acid and P4 is arginine. Furthermore, in this embodiment P1 and/or P2 and/or P3 are an amino acid reside other than proline.

In another embodiment P1' is homophenylalanine. In a yet further, or preferred, embodiment, P1 is Gly.

The MMP proteolytic cleavage site, Y, may comprise the amino acid sequence (iv)

-Hof-Gly- (iv)

The MMP proteolytic cleavage site, Y, may comprise the amino acid sequence (v)

-P2'-Hof-Gly-P2- (v)

wherein P2 and P2' are as defined herein.

The MMP proteolytic cleavage site, Y, may comprise the amino acid sequence (vi)

-P2'-Hof-Gly-P2-P3-P4- (vi)

wherein P2' to P4' and P2 are as defined herein. Preferably P4 is arginine.

Preferably P3 is not proline.

In an embodiment the invention provides a compound of formula (I) wherein Y comprises the sequence -Leu-Tyr-Hof-Gly-Cit-Ser-Arg-. (SEQ ID NO: 1).

In a further embodiment the invention provides a compound of formula (I) wherein Y does not include the sequence -Leu-Gly-Leu-Pro- wherein cleavage takes place between Leu-Gly residues.

The invention may provide a compound of formula (I) wherein the cleavage site, Y, comprises a sequence of amino acids in which one or more amino acids in the sequence are glycosylated to enhance hydrophilicity and as such solubility. Glycosylation of residues may be as follows:

O-glycosylation of amino acids in the sequence through the side-chains of serine, threonine, tyrosine;

N-glycosylation of amino acids in the sequence through the side-chains of aspartic acid, glutamic acid; and/or S-glycosylation of amino acids in the sequence through cysteine.

The invention may provide a compound of formula (I) wherein the cleavage site, Y, comprises a sequence of amino acids in which one or more amino acids in the sequence are phosphorylated to enhance hydrophilicity and as such solubility. Suitable amino acids include Serine, Threonine, Tyrosine. In an embodiment of the invention there is provided a compound of formula (I) wherein Y comprises the sequence (i) (ii) or (iii) in which P2', for example tyrosine, is phosphorylated.

In a further embodiment of the invention there is provided a compound of formula (I) wherein Y comprises the sequence (i) (ii) or (iii) in which P3, and optionally P2', is/are phosphorylated amino acids.

The invention also provides a compound of formula (I) wherein the cleavage site, Y, includes a peptide analogue, for example a peptide mimic, in which, by way of example an amide bond is replaced with olefinic bonds, Nα- and/or Cα-methylated amino acids, unnatural amino acids and other approaches known in the art. Such peptidomimetic approaches are used in the art to enhance the specificity of cleavage thereby serving to diminish undesired enzymatic hydrolysis. In an embodiment of the invention Y includes an analogue wherein one or more amide bonds within the amino acid sequence are replaced with Nα- and/or Cα-methylated amino acids.

An embodiment the invention comprises a compound of formula (I) wherein Y comprises a C-terminal site and an N-terminal site and wherein said C-terminal site is directly or indirectly linked to X and said N-terminal site is directly or indirectly linked to a further moiety for example c or Z as described hereinbelow.

An alternative embodiment of the invention comprises a compound of formula (I) wherein Y comprises a C-terminal site and an N-terminal site and wherein said N-terminal site is directly or indirectly linked to X and said C-terminal site is directly or indirectly linked to a further moiety for example c or Z as described hereinbelow.

In one preferred embodiment the invention there is provided a compound of formula (I) wherein X is colchicine or an analogue thereof and Y is a peptide comprising the amino acid sequence (i), (ii), (iii), (iv), (v) or (vi) as defined herein.

In a preferred aspect the invention provides a compound of formula (II)

X—Y-*c* (II)

wherein X and Y are as defined herein;

c is an end group or "capping group". Capping groups may be used to cap a peptide chain in pharmaceutical use in order to prevent non-specific degradation of the peptide for example by enzymes other than MMPs. c may include any appropriate moiety on the N- or C-terminus acting as a blocking group selected from the group including, but not limited to, aliphatics, aromatics, polycyclics, carbohydrates (e.g. simple sugars), amino acids (including D-amino acids). To improve solubility, c may be a hydrophilic group for example any of the aforementioned bearing additional polar functional groups (e.g. acids, amines, alcohols, phenols). c may be represented by the formula $(c)_n$ wherein n is an integer between 1 and 5. In an embodiment of the invention, c is represented $(c)_n$ wherein c is an amino acid (e.g. a non-natural amino acid) and n is 3 In an embodiment of the invention c is not serine where n is 3. In a further embodiment c is not serine or quinic acid.

The present invention may further provide a "linker". The linker may be provided at the C and/or N terminus of Y. Preferably the linker is provided at the C terminus of Y. Preferably the linker is continuous with the amino acid sequence of Y. The linker may include any moiety that is associated with Y and which may be removed chemically, enzymatically or decompose spontaneously. The linker may consist of a single amino acid (e.g. tyrosine) or may comprise an amino acid sequence. Where the linker comprises a sequence of amino acids, the sequence may provide a hydrophilic region that may facilitate cleavage by an MMP at Y. O-glycosylation of suitable amino acids in the sequence namely serine, threonine and tyrosine may enhance hydrophilicity and as such solubility.

Thus in a preferred aspect of the invention there is provided a compound of formula (III)

X-*a*-Y (III)

wherein X and Y are as defined herein; and a is a linker wherein the linker is directly or indirectly associated with X.

In an embodiment the invention provides a compound of formula (IV)

X-*a*-Y-*c* (IV)

wherein X, a, Y and c are as defined herein.

In a yet further preferred aspect of the invention there is provided a "spacer" which may be the same as, or different to, the linker described herein. The spacer may be provided at the C and/or N terminal of Y. Preferably the spacer is provided at the N terminus of Y and serves to prevent unwanted removal of c during synthesis. The spacer may be directly or indirectly associated with Y. The spacer may include any single amino acid (e.g. β-alanine), amino acid sequence, a succinyl group. Thus the invention preferably provides a compound of formula (V)

X—Y-*b*-*c* (V)

wherein X, Y, and c are as defined herein;

b is a spacer as defined herein.

In a further embodiment the invention provides a compound of formula (VI)

X-*a*-Y-*b*-*c* (VI)

wherein X, Y, a, b and c are as defined herein.

In one embodiment of the invention there is provided a compound of formula (VI) wherein X is colchicine (or an analogue thereof), Y is a peptide comprising the amino acid sequence (i), (ii), (iii), (iv), (v) or (vi) as defined herein, a is tyrosine and b is alanine.

In a second aspect of the invention there is provided a compound, or pharmaceutically acceptable salt thereof, of formula (VII)

X—Y—Z (VII)

wherein X and Y are as defined herein; Z is an anti-cancer agent.

Preferably Z is an anticancer agent selected from the group consisting of a vascular disrupting agent, which may the same as or different to X, an antimetabolite (e.g. 5-fluorouracil), a cytotoxic or anti-proliferative agent (e.g. anthracycline (e.g doxorubicin), vinca alkaloid, taxane, cytotoxic nucleotide), a biotoxin, radiotherapeutic, hormonal agent or any natural products or agents known to induce a cytotoxic, cytostatic, anti-angiogenic or vascular disrupting effect.

In a preferred aspect of the invention there is provided a compound of formula (VIII)

X-*a*-Y—Z (VIII)

wherein X, a, Y and Z are as defined herein.

In a yet preferred aspect of the invention there is provided a compound of formula (IX)

X-*a*-Y-*b*-Z (IX)

wherein X, a, Y, b and Z are as defined herein. In this aspect of the invention, the purpose of the spacer b is to convert the N-terminal amine of Y into a carboxylic acid to allow attachment of a compound Z wherein Z bears a free amine (for example where Z is doxorubicin). Where Z bears a free carboxylic acid, b is not required.

In a preferred aspect of the invention there is provided a compound of formula (VII) wherein X is colchicine or a derivative thereof for example azademethylcolchicine and Z is a cyctotoxic agent for example doxorubicin. Preferably still Y is a peptide comprising the amino acid sequence (i), (ii), (iii), (iv), (v) or (vi) as defined herein.

In a further preferred aspect of the invention there is provided a compound of formula (VII) wherein X and Z are selected from colchicine or an analogue or derivative thereof. Also provided is a compound of the invention wherein X and Z may both be colchicine. In this aspect, Y may be a peptide comprising the amino acid sequence (i), (ii), (iii), (iv), (v) or (vi) as defined herein.

Compounds according to the invention may be prepared by solid-phase, for example attached to a polymeric support, or solution-phase synthesis for example in the presence of a coupling agent or using a convergent synthesis.

Thus a further aspect of the invention provides a process for preparing a compound according to the invention the process comprising the steps of i) providing a solid support attached to X;

ii) optionally attaching a linker a to the C or N terminal of X;

iii) attaching amino acid residues step-wise to the C or N terminal of X, or the linker attached to X in (ii), to provide the peptide sequence Y containing the MMP proteolytic cleavage sequence;

iii) optionally attaching a capping group c to the respective C or N terminal of Y to provide a compound of formula (II) or (IV).

In a preferred process the solid support is any polymeric support such as any polystyrene based or PEG based resin for example trityl-based resins. The linker may be a succinate or malonate derivative for example succinic anhydride.

A yet further aspect of the invention provides a process for preparing a compound according to the invention the process comprising the steps of i) preparing peptide sequence Y;

ii) attaching a capping group c to the respective C or N terminal of Y;

iii) preparing a solution of X and the capped peptide prepared in (ii) in the presence of a coupling agent and isolating the desired compound.

In a preferred process Y is prepared by the step wise attachment of amino acids to a solid support to provide a peptide sequence. Alternatively, sequence Y may be synthesised in solution.

Any coupling agent known in the art may be used in a process of the invention for example EDAC, DCC, DiC, PyBOP, HCTU etc in a suitable solvent (e.g. DMF, THE etc.

In an alternative solution phase synthesis, one or more amino acids of the C-terminus of sequence Y may be conjugated to X in solution, to allow the remainder of the peptide sequence (e.g. pre-synthesised on a solid support as described previously) to be conjugated in solution in a convergent synthesis.

A preferred process of the invention provides for the attachment of X to the C terminus of Y. Furthermore the process may include the attachment of Z to the N-terminus of Y. For example the process may comprise the steps of:

i) introduction of an amine group to X for attachment to the C terminus of Y; and optionally ii) introduction of a carboxylic acid group (or isothiocyanate or isocyanate group) to Z for attachment to the N terminus of Y.

A further preferred process provides for the attachment of X to the N-terminus of Y.

Furthermore the process may include the attachment of Z to the C-terminus of Y. For example the process may comprise the steps:

i) introduction of a carboxylic acid group (or isothiocyanate or isocyanate group) to X for attachment to the N terminus of Y; and optionally ii) introduction of a amine group to Z for attachment to the C terminus of Y.

In a preferred process of the invention, X is colchicine or an analogue or derivative thereof e.g. azademthylcolchicine and Z is a cytotoxic agent e.g. doxorubicin.

In a further aspect the invention provides the use of a MMP proteolytic cleavage site, in particular an MT-MMP specific cleavage site such as defined herein, in the site specific activation of a VDA. The term "site specific activation" as used herein means, in general terms and not limited to, the activation of a VDA by site specific cleavage at the MMP proteolytic cleavage site. Site specific cleavage at the proteolytic cleavage site is expected to take place concomitantly with the release and hence activation of the VDA.

Pharmaceutical Compositions and Uses other aspects the invention provides a compound, or pharmaceutically acceptable salt thereof, as hereinbefore described for use in medicine. In further aspects, there is provided a pharmaceutical formulation comprising a compound as hereinbefore described. The formulation may contain at least one additional pharmaceutically acceptable component e.g. an excipient, diluent or carrier. Preferably the formulation is intended for parenteral administration.

The invention provides a pharmaceutical formulation comprising a compound according to the invention. In a preferred embodiment, the compound is of formula (VII).

In a preferred aspect of the invention said composition includes a pharmaceutically acceptable carrier or diluent.

The compositions of the invention are typically administered in effective amounts. An "effective amount" is that amount of a composition that alone, or together with further doses, produces the desired response. When administered, the pharmaceutical compositions of the present invention are administered in pharmaceutically acceptable preparations. Such preparations may routinely contain pharmaceutically acceptable concentrations of salt, buffering agents, preservatives, compatible carriers and optionally other therapeutic agents (for example, cisplatin; carboplatin; cyclosphosphamide; melphalan; carmusline; methotrexate; 5-fluorouracil; cytarabine; mercaptopurine; daunorubicin; doxorubicin; epirubicin; vinblastine; vincristine; dactinomycin; mitomycin C; taxol; L-asparaginase; G-CSF; etoposide; colchicine; derferoxamine mesylate; and camptothecin).

The compositions of the invention can be administered by any conventional route, including injection or by gradual infusion over time. The administration may, for example, be oral, intravenous, intraperitoneal, intramuscular, intracavity, subcutaneous, or transdermal. In the case of treating a particular disease, such as cancer, the desired response is inhibiting the progression of the disease. This may involve only slowing the progression of the disease temporarily, although more preferably, it involves halting the progression of the disease permanently. This can be monitored by routine methods known in the art.

Administration of the compositions to mammals other than humans, (e.g. for testing purposes or veterinary therapeutic purposes), is carried out under substantially the same conditions as described above. A subject, as used herein, is a mammal, preferably a human, and including a non-human primate, cow, horse, pig, sheep, goat, dog, cat or rodent.

When administered, the pharmaceutical preparations of the invention are applied in pharmaceutically-acceptable amounts and in pharmaceutically-acceptable compositions. The term "pharmaceutically acceptable" means a non-toxic material that does not interfere with the effectiveness of the biological activity of the active ingredients.

Pharmaceutical compositions may be combined, if desired, with a pharmaceutically-acceptable carrier. The term "pharmaceutically-acceptable carrier" as used herein means one or more compatible solid or liquid fillers, diluents or encapsulating substances which are suitable for administration into a human. The term "carrier" denotes an organic or inorganic ingredient, natural or synthetic, with which the active ingredient is combined to facilitate the application.

The pharmaceutical compositions may contain suitable buffering agents, including: acetic acid in a salt; citric acid in a salt; boric acid in a salt; and phosphoric acid in a salt.

The pharmaceutical compositions also may contain, optionally, suitable preservatives, such as: benzalkonium chloride; chlorobutanol; parabens and thimerosal. Compositions suitable for oral administration may be presented as discrete units, such as capsules, tablets, lozenges, each containing a predetermined amount of the active compound. Other compositions include suspensions in aqueous liquids or non-aqueous liquids such as syrup, elixir or an emulsion.

Compositions suitable for parenteral administration conveniently comprise a sterile aqueous or non-aqueous preparation of compound, which is preferably isotonic with the blood of the recipient. This preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1, 3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulation suitable for oral, subcutaneous, intravenous, intramuscular, etc. administrations can be found in Remington's Pharmaceutical Sciences, Mack Publishing Co., Easton, Pa.

The compounds according to the invention may be used to treat a disease or condition associated with tissue over-expressing an MMP, in particular a MT-MMP. Thus the invention provides a method to treat cancer in a subject comprising administering an effective amount of a compound according to the invention. In a preferred method of the invention said subject is human.

As used herein, the term 'cancer' refers to cells possessing the capacity for autonomous growth i.e., an abnormal state or condition characterised by rapidly proliferating cell growth. The term is meant to include all types of cancerous growths or oncogenic processes, metastatic tissues or malignantly transformed cells, tissues, or organs, irrespective of histopathological type or stage of invasiveness. The term 'cancer' includes malignancies of epithelial, endodermal and mesenchymal origin, particularly carcinomas and sarcomas, such as those affecting the respiratory system (mouth, nose, trachea, lung), gastrointestinal tract (tongue, esophagus, stomach, small intestines, colon, liver, pancreas, gall bladder, rectum), endocrine system (thyroid, pituitary, adrenal glands), genito-urinary tract (urinary bladder, kidney), reproductive system (breast, ovaries, uterus, cervix, prostate, penis, scrotum, testes), skin (melanocytes, epidermis, endodermis), nervous system (brain, spinal cord, glial cells, neurons) and lymphoid system.

The term 'carcinoma' is art recognised and refers to malignancies of epithelial origin including respiratory system carcinomas, gastrointestinal system carcinomas, endocrine system carcinomas, genito-urinary tract carcinomas, skin carcinomas, and carcinomas of the reproductive system. The term "carcinoma" also includes "adenocarcinomas" referring to carcinomas deriving from glandular tissue, "squamous carcinomas" referring to carcinomas of squamous origin, and "carcinosarcomas" referring to tumours composed of carcinomatous and sarcomatous tissue. Exemplary carcinomas include those forming from the epithelia of the cervix, prostate, breast, nose, head and neck, oral cavity, esophagus, stomach, liver, pancreas, colon, ovary, urinary bladder and lung, particularly non-small lung carcinoma.

The term 'sarcoma' is art recognised and refers to malignancies of soft tissues or connective or supportive tissue, including bone, cartilage, adipose tissue, smooth muscle, skeletal muscle, nerve sheath, blood vessels, mesothelium, and gastrointestinal stroma. Further types of cancer include "leukaemias" which refer to tumours deriving from white blood cells, and "lymphomas" referring to tumours of the lymphoid system.

A pharmaceutical formulation comprising a compound according to the invention may be administered in combination, either sequentially or at a substantially similar time, as an anti-cancer agent (chemotherapeutic agent) including, but not limited to, an antimetabolite (e.g. 5-fluorouracil), a cytotoxic or anti-proliferative agent (e.g. anthracycline, vinca alkaloid, taxane, cytotoxic nucleotide), a biotoxin, radiotherapeutic, hormonal agent or any natural products or agents known to induce a cytotoxic, cytostatic, anti-angiogenic or vascular disrupting effect.

As used herein, "treatment" refers to clinical intervention in an attempt to alter the natural course of the individual or cell being treated, and may be performed either for prophylaxis or during the course of clinical pathology.

In a further aspect the invention provides the use of a compound according to the invention in the manufacture of a medicament to treat cancer.

In one aspect of the present invention the compounds or compositions of the invention may be used to treat an inflammatory disorder and/or an inflammatory response. Thus, according to a further of the invention there is provided a method to treat an inflammatory disorder in a subject comprising administering an effective amount of a compound according to the invention.

The inflammatory disorder may be selected from the group consisting of consisting of atherosclerosis, rheumatoid arthritis, osteoarthritis, gout, lupus erythematosus, scleroderma, Sjorgen's syndrome, poly- and dermatomyositis, vasculitis, tendonitis, synovitis, bacterial endocarditis, periodontitis, osteomyelitis, psoriasis, pneumonia, fibrosing alveolitis, chronic bronchitis, bronchiectasis, emphysema, silicosis, pneumoconiosis, tuberculosis, ulcerative colitis, Crohn's disease, chronic inflammatory demyelinating polyradiculoneuropathy, chronic inflammatory demyelinating polyneuropathy, multiple sclerosis, Guillan-Barre Syndrome and myasthemia gravis, mastitis, laminitis, laryngitis, chronic cholecystitis, Hashimoto's thyroiditis, and inflammatory breast disease. In one embodiment, the inflammatory disorder may be the result of tissue or organ rejection after transplantation. In particular embodiments the inflammatory disorder is selected from the group consisting of atherosclerosis, rheumatoid arthritis, osteoarthritis, sepsis and polyarthritis.

The compounds of the invention may be used to treat heart failure. Also provided is a use of a compound as described herein for the manufacture of a medicament to treat heart failure.

In one embodiment of the present invention the compounds of the invention may be useful in treating a wound (e.g. ulcers, lesions including cutaneous cuts or burns). Thus the invention provides a method to treat a wound in a subject comprising administering an effective amount of a compound according to the invention. In a preferred method of the invention said subject is human.

The compounds of the invention may also be used to treat conditions and disorders associated with menstruation.

There is further provided a package or kit of parts comprising:

(1) a compound or composition described herein; together with (2) instructions to use the compound in a method or use described herein.

The package defined herein may comprise more than one dosage unit in order to provide for repeat dosing. If more than one dosage unit is present, such units may be the same, or may be different in terms of the dose of the compound composition and/or physical form.

The extent of protection includes counterfeit or fraudulent products which contain or purport to contain a compound of the invention irrespective of whether they do in fact contain such a compound and irrespective of whether any such compound is contained in a therapeutically effective amount.

Included in the scope of protection are packages which include a description or instructions which indicate that the package contains a species or pharmaceutical formulation of the invention and a product which is or comprises, or purports to be or comprise, such a formulation or species. Such packages may be, but are not necessarily, counterfeit or fraudulent.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

Materials and Methods

Example 1

Synthesis of Immobilised Colchicine Derivative, Azademethylcolchicine:

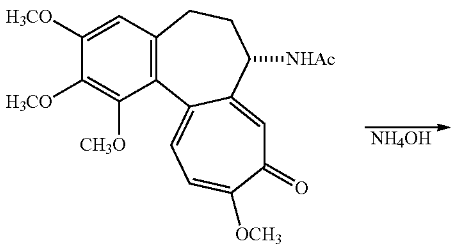

colchicine

-continued

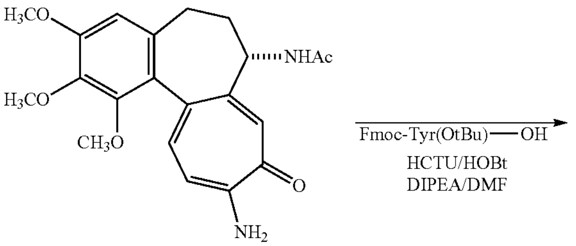

1

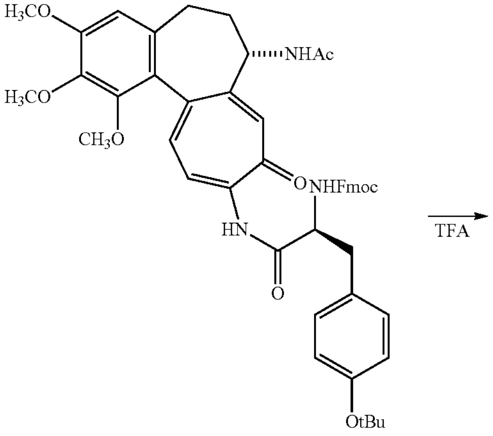

2

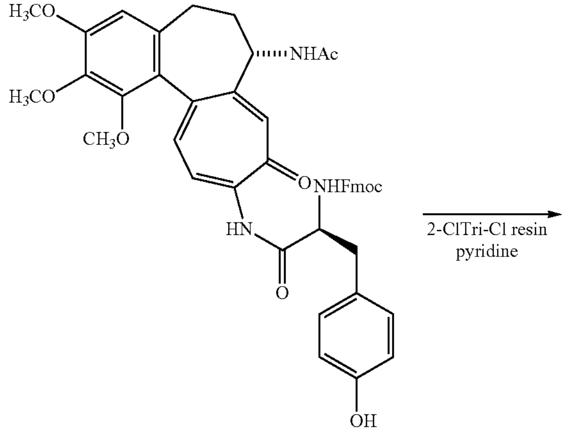

3

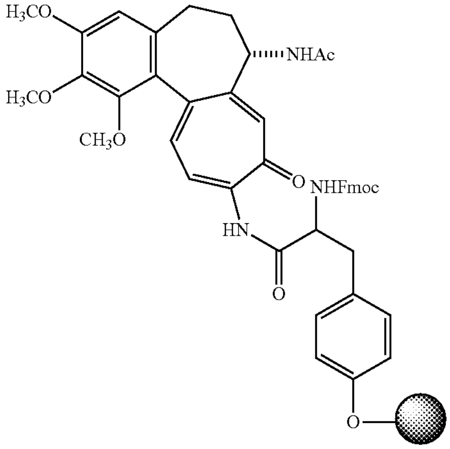

4

Synthesis of 1:

Ammonia solution (35%, 15 mL) was added to colchicine (750 mg, 1.88 mmol, 1.00 eq) and the reaction mixture stirred at room temperature overnight. The crude product was washed with $KHSO_4$ (1M, aq), dried with $MgSO_4$, filtered and concentrated under reduced pressure. It was subsequently purified by flash chromatography on silica gel (gradient elution: $CH_2Cl_2$/methanol 95:5 to 10:1) to give 1 as a yellow solid (427 mg, 1.11 mmol, 59%).

$\delta_H$ (600 MHz, $CDCl_3$), 7.99 (1H, broad s, NH), 7.56 (1H, d, J 2.1, C8-H), 7.32 (1H, d, J 10.7, C11-H), 6.88 (1H, d, J 11.0, C10-H), 6.52 (1H, s, C4-H), 6.03 (2H, broad s, $NH_2$), 4.68 (1H, ddd, J 12.6, 6.5 and 6.5, C7-H), 3.93 (3H, s, $OCH_3$), 3.88 (3H, s, $OCH_3$), 3.60 (3H, s, $OCH_3$), 2.47 (1H, dd, J 13.4 and 6.2, C5-$CH_2$), 2.35 (1H, ddd, J 13.4, 12.7 and 6.9, C5-$CH_2$), 2.29-2.23 (1H, m, C6-$CH_2$), 1.98 (3H, s, $CH_3$), 1.90-1.88 (1H, m, C6-$CH_2$); ES m/z (%) 385 [$M^+$+H](100).

Synthesis of 2:

HCTU (642 mg, 1.55 mmol, 1.50 eq) and diisopropylethylamine (DiPEA, 516 μL, 404 mg, 3.11 mmol, 3.00 eq) were added to a solution of Fmoc-tyr(tBu)-OH (714 mg, 1.55 mmol, 1.50 eq) in DMF (10 mL). After stirring at room temperature for 5 minutes, 1 (398 mg, 1.04 mmol, 1.00 eq) was added to the solution. The reaction mixture was stirred at 50° C. for 22 h. DMF was removed in vacuo and the resultant oil was dissolved in $CH_2Cl_2$ (20 mL). The organic phase was washed with $KHSO_4$ (aq, 2×20 mL), dried with $MgSO_4$ and concentrated under reduced pressure. The crude product was purified by flash chromatography (gradient elution: $CH_2Cl_2$/methanol 100:0 to 99:1 to 98:2) to give 2 as a yellow solid (530 mg, 642 μmol, 67%).

$\delta_H$ (600 MHz, $CDCl_3$), 10.42 (1H, broad s, NH), 9.02 (1H, d J 10.7, C11-H), 7.75 (2H, d, J 7.2, C23-H, C24-H), 7.54 (2H, d, J 7.2, C20-H, C27-H), 7.45 (1H, d, J 11.0, C10-H), 7.39 (2H, dd, J 7.2 and 7.2, C22-H, C25-H), 7.29 (2H, dd, J 6.6 and 6.6, C21-H, C26-H), 7.19 (1H, broad s, C8-H), 7.03 (2H, d, J 7.9, C14-H, C17-H), 6.81 (2H, d, J 7.9, C15-H, C16-H), 6.50 (1H, s, C4-H), 5.88 (1H, broad s, NH), 5.25 (1H, broad s, C12-H), 4.73-4.67 (1H, m, C7-H), 4.43 (1H, dd, J 10.0 and 7.6, C18-$CH_2$), 4.28 (1H, dd, J 10.0 and 7.2, C18-$CH_2$), 4.16 (1H, dd, J 7.2 and 6.19, C19-H), 3.93 (3H, s, $OCH_3$), 3.88 (3H, s, $OCH_3$), 3.62 (3H, s, $OCH_3$), 3.21 (1H, dd, J 13.1 and 4.8, C13-$CH_2$), 3.11 (1H, dd, J 13.1 and 5.5, C13-$CH_2$), 2.53 (1H, dd, J 13.4 and 6.2, C5-$CH_2$), 2.40 (1H, ddd, J 13.4, 12.7 and 6.9, C5-$CH_2$), 2.22-2.15 (1H, m, C6-$CH_2$), 1.88 (3H, s, $CH_3$), 1.80 (1H, ddd, J 11.5, 11.3 and 6.9, C6-$CH_2$), 1.22 (9H, s, $C(CH_3)_3$); ES m/z (%) 826 [$M^+$](100).

Synthesis of 3:

TFA (2 mL) was added to a solution of 2 (486 mg, 589 μmol, 1.00 eq) and the reaction mixture stirred for 20 min. TLC indicated quantitative conversion to the product. The product was concentrated under reduced pressure, with toluene co-evaporation to give 3 in quantitative yield.

$\delta_H$ (600 MHz, $CDCl_3$), 10.08 (1H, broad s, NH), 8.99 (1H, d J 10.7, C11-H), 7.71 (2H, d, J 6.2, C23-H, C24-H), 7.55 (1H, s, C8-H), 7.49 (2H, dd, J 6.5 and 6.5, C20-H, C27-H), 7.41 (1H, d, J 10.2, C10-H), 7.33 (2H, dd, J 6.2 and 6.2, C22-H, C25-H), 7.26-7.21 (2H, m, C21-H, C26-H), 6.91 (2H, d, J 8.3, C14-H, C17-H), 6.56 (2H, d, J 7.2, C15-H, C16-H), 6.45 (1H, s, C4-H), 5.93 (1H, broad s, NH), 5.28 (1H, s, NH), 4.95-4.90 (1H, m, C12-H), 4.60 (1H, ddd, J 11.7, 5.8 and 6.9, C7-H), 4.39 (1H, dd, J 8.9 and 8.6, C18-$CH_2$), 4.29-4.24 (1H, m, C18-$CH_2$), 4.12 (1H, dd, J 6.9 and 6.9, C19-H), 3.90 (3H, s, $OCH_3$), 3.84 (3H, s, $OCH_3$), 3.54 (3H, s, $OCH_3$), 3.08 (2H, d, J 5.2, C13-$CH_2$), 2.44 (1H, dd, J 13.4 and 6.2, C5-$CH_2$), 2.33-2.26 (1H, m, C5-$CH_2$), 2.15-2.09 (1H, m, C6-$CH_2$), 1.82 (3H, s, $CH_3$), 1.75-1.69 (1H, m, C6-$CH_2$); ES m/z (%) 770 [$M^+$](100).

Preparation of 4:

2-Chlorotrityl chloride resin (Novabiochem, 100-200 mesh, substitution 1.4 $mmolg^{-1}$, 589 mg, 0.765 mmol, 1.00 eq) was suspended in a solution of 3 (589 mg, 0.765 mmol, 1.00 eq), dimethylaminopyridine (10 mg, 76.5 μmol, 0.01 eq), DiPEA (247 mg, 1.913 mmol, 333 μL, 2.50 eq) and pyridine (241 mg, 3.061 mmol, 248 μL, 4.00 eq) in THF (10 mL) and stirred for 6 hours at 50° C. The resin was subsequently filtered and washed thoroughly with THF. The resin was then capped by washing the resin carefully with methanol ($CH_2Cl_2$:MeOH:DiPEA 17:2:1, 100 mL). Resin 4 was dried overnight over $P_2O_5$. Dry resin weight: 593 mg (loading 56%).

General Procedure for Synthesis of Endopeptidase-Activated Pro-Drugs isothiocyanate (2.50 eq, in the presence of DiPEA, 1.50 eq). The success of this reaction was also monitored by the Kaiser test.

An additional β-alanine residue was incorporated into the sequence to overcome incompatability of the thiourea linkage and the acidic conditions of cleavage (the thiourea can rearrange, and the carbonyl carbon of the preceding amide bond can undergo nucleophilic attack by the sulphydryl-like function so formed. This leads to cleavage of the amide bond, with concomitant formation of a cyclic thiazolinone. The thiazolinone can undergo rearrangement in the presence of aqueous acid to form a thiohydantoin).

On completion of the sequence, the resin was washed (DMF, CH2C12, CH2C12/MeOH) and dried in vacuo over KOH to constant weight. Peptides were cleaved from the resin by mild acidolysis using TFA-H2O-triisopropylsilane 95:2.5:2.5 for 2 h at RT, with simultaneous sidechain deprotection. Following cleavage, the TFA was removed under (SEQ ID NO: 2)

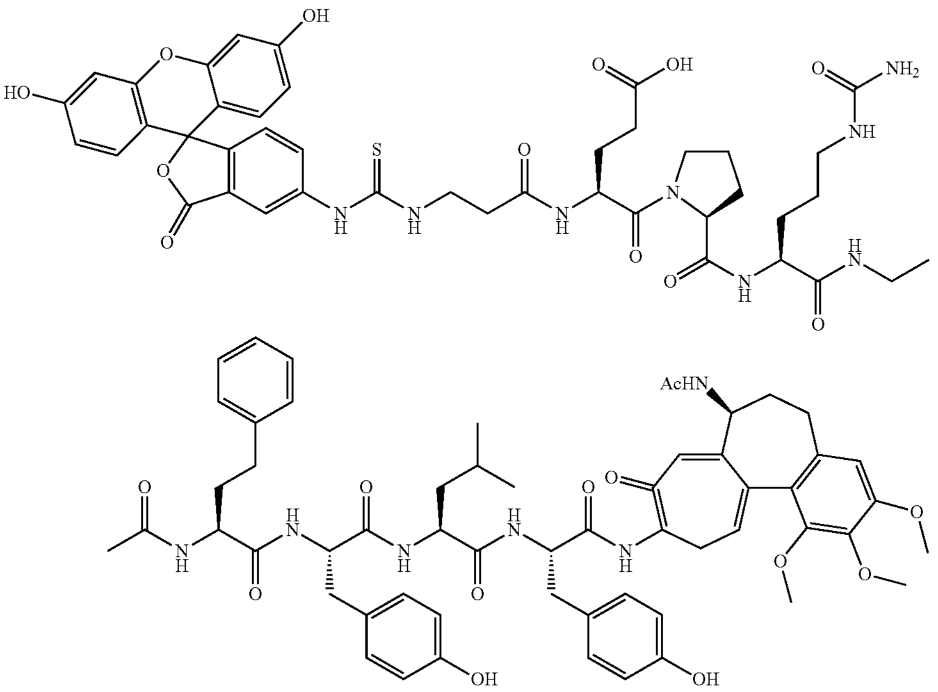

5 fluo-bala-glu-pro-cit-gly-hof-tyr-leu-tyr-colch

As an example, peptide conjugate 5 was synthesised using conventional solid phase peptide synthesis, from immobilised colchicine derivative 4, using an Fmoc-based strategy.

Nα-Fmoc strategy synthesis was achieved manually using 2-hlorotrityldderivatised resin. The resin was swelled thoroughly in DMF, followed by removal of the NFmoc protecting group by treatment with 20% v/v piperidine in DMF (3×3 min). All couplings were performed in DMF, employing 2.5-fold molar excesses of Nα-Fmoc protected amino acids (with appropriate side-chain protecting groups), and activated using HCTU/HOBt/DiPEA. Nα-Fmoc deprotections were performed using 20% piperidine in DMF (3×3 min). The success of couplings and deprotections was monitored using the ninhydrinbased Kaiser test. Unsuccessful couplings were repeated. After the final Nα-Fmoc deprotection, the peptide chain was endcapped with fluorescein reduced pressure. The crude product was extracted into 95% aqueous acetic acid and lyophilised. Crude peptide was subsequently analysed using reversed phase HPLC and purified using preparative HPLC (purity >97%). Pure fractions were combined and lyophilised. A C18 preparative column (Zorbax Eclipse, 21.2×150 mm XDB-C18, Agilent) was used for peptide conjugate purification. Mobile phases were as follows; Mobile Phase A: HPLC grade water and 0.045% TFA. Mobile Phase B consisted of 10% HPLC grade water, 90% acetonitrile and 0.045% TFA. Mobile phase was degassed by vacuum filtration through a 0.45 μm pore cellulose nitrate filter (Sartolon, Sartorius, UK). Chromatography was performed at room temperature and the flow rate maintained at 21.2 ml/min. Mobile phase gradients were optimised and scaled up from a gradient previously designed in-house for structurally similar compounds. UV absorbance detection was optimal at 255 nm. ES m/z (%) 951.8 [M+H]

2+(100). RP-HPLC (Gradient: 0 min 30% B; 5 min 35% B; 25 min 80% B; 26 min 100% B; 27 min 100% B; 30 min 30% B) Rt=11.98 min.

Attachment of Colchicine to a Peptide Sequence Through its B-Ring to the Peptide N-Terminus To enable attachment of a colchicine moiety through the peptide N-terminus, the following strategy will be used. The B-ring amine can be de-masked using published methods. Acylation with aspartic acid will introduce a carboxylic acid to the molecule (from the amino acid side chain) thereby enabling conjugation to the free amine at the

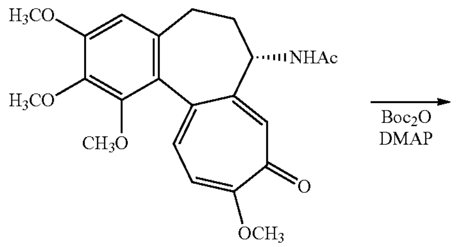

colchicine

-continued

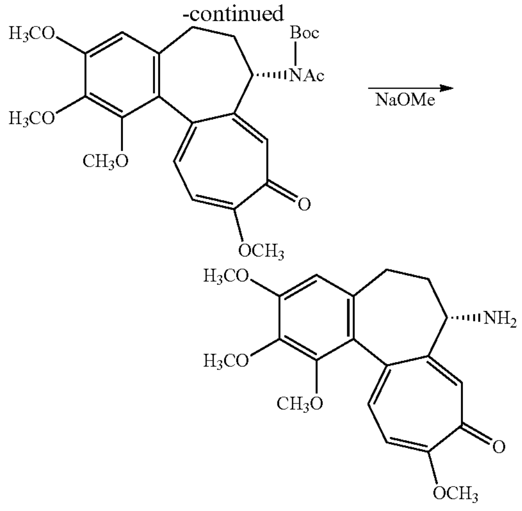

peptide N-terminus (see below).

Acetylation of the amide bond will also be examined, to assess whether parent colchicine is released following MMP activation and subsequent exopeptidase degradation.

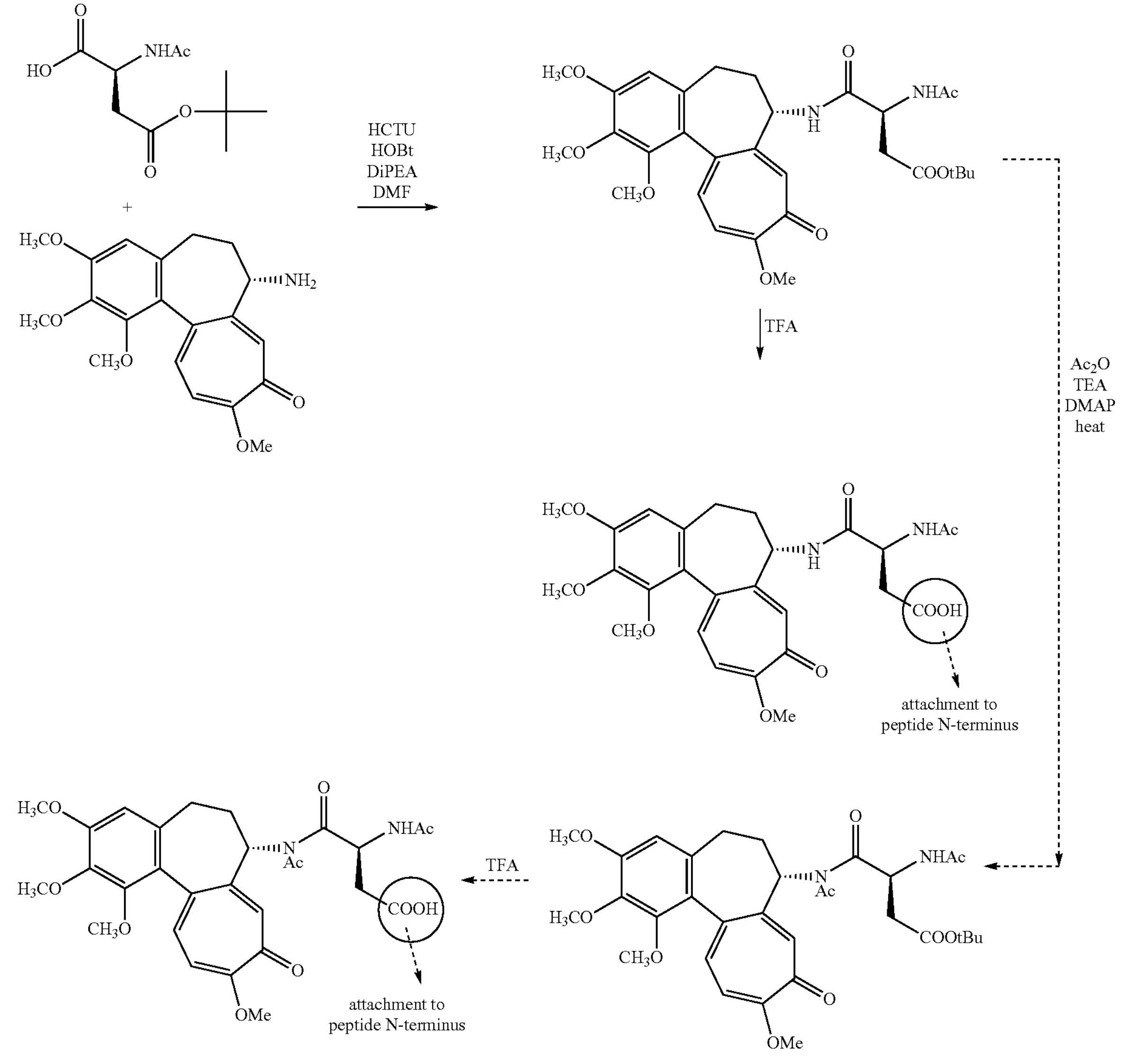

Attachment of Colchicine Analogue to a Peptide Sequence Through its C-Ring to the Peptide N-Terminus To enable attachment of a colchicine analogue through its N-terminus, the following strategy will be used. Acylation of azademethylcolchicine can be effected as described previously. On de-masking of the Boc-protecting group, acylation with succinic anhydride (or a mono-protected succinate or malonate (or similar) derivative) follows. Deprotection will then afford a carboxylic acid functionality suitable for attachment to the peptide N-terminus.

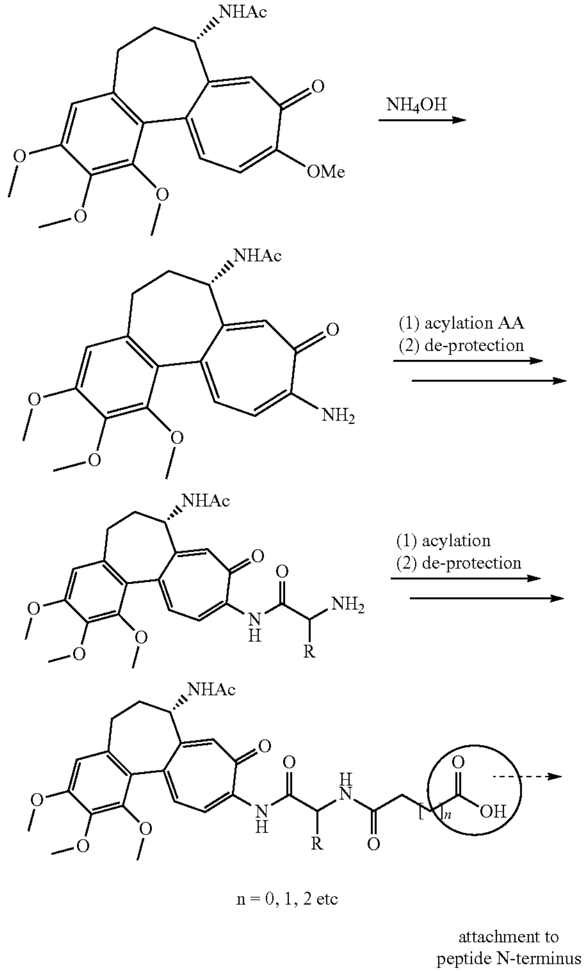

Strategies for the Attachment of Doxorubicin to a Peptide Sequence:

N-Terminal Doxorubicin Linkage

To enable attachment of doxorubicin through the peptide N-terminus (following peptide synthesis using the immobilised colchicine derivatised resin previously described) it must first be modified to introduce a carboxylic acid. Examples include reaction with succinic anhydride (strategy 1, below). However, by utilising the side chain of aspartic acid (both natural amino acids), as shown below (strategy 2) a natural amino acid (as opposed to a foreign chemical entity) is released on metabolism:

Strategy 1: (Succinyl Spacer)

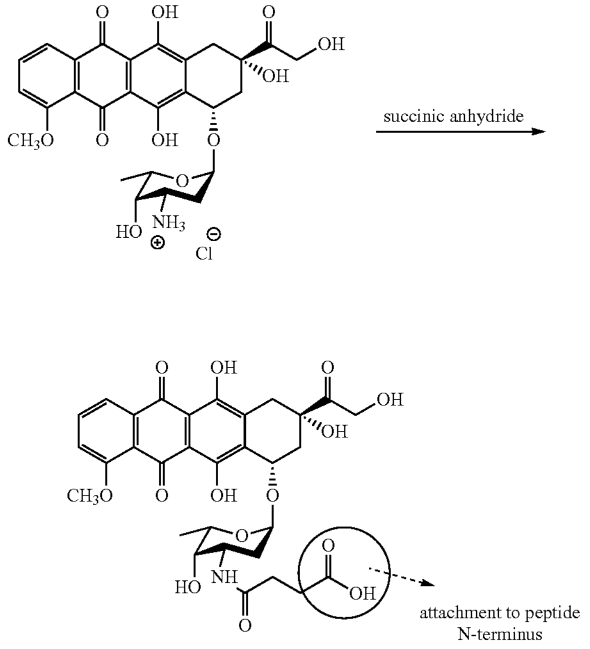

Strategy 2: (Amino Acid Spacer)

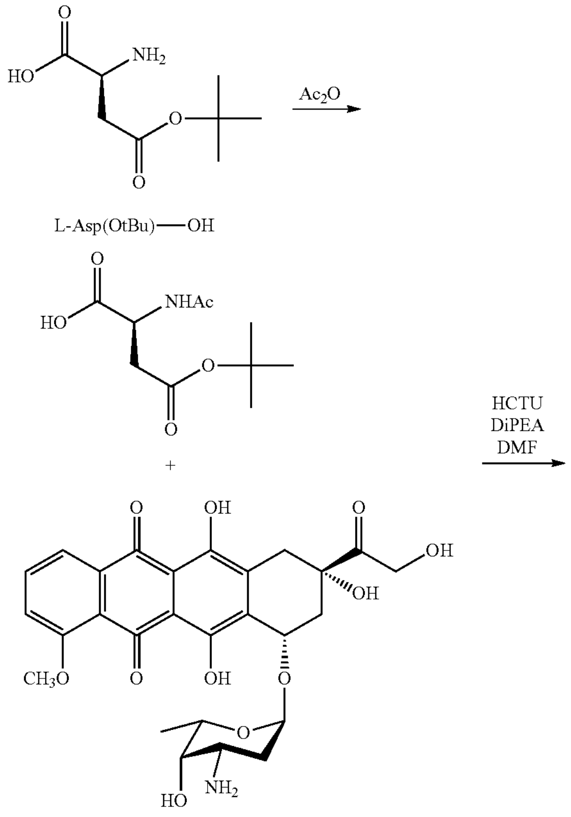

-continued

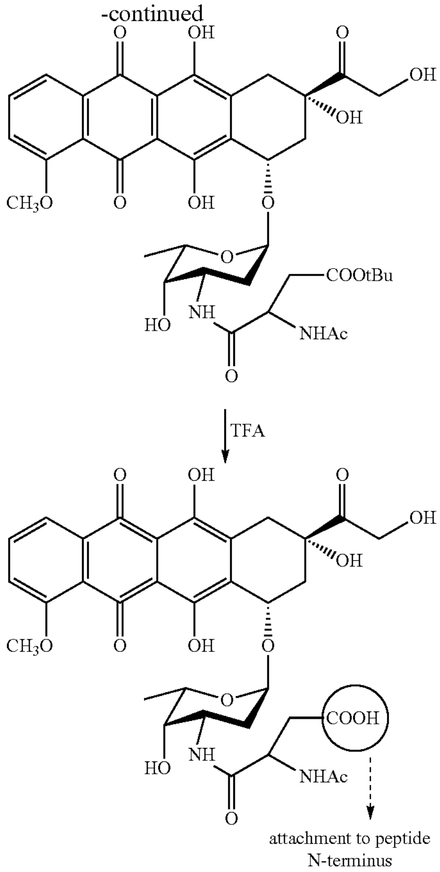

Strategy 3

In a manner analogous to that described in Strategies 1 and 2 the doxorubicin sugar amine can be acylated by an amino acid, which on de-protection can be further derivatised by a succinate (or otherwise) spacer to yield a derivative which can be attached to the peptide N-terminus.

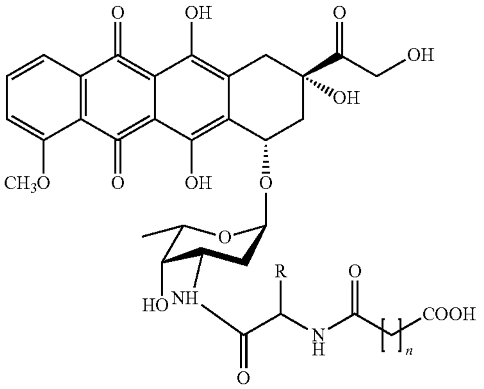

n = 1, n = 2

2) C-Terminal Doxorubicin Linkage

Protection of the amine group of doxorubicin with Dde (a commonly used protecting group in peptide chemistry and by our group) would allow immobilisation of the agent onto a trityl-based (or otherwise) resin. Subsequent removal of the Dde group would de-mask the amine, allowing a peptide sequence to be constructed from this point (i.e. through the C-terminus). Standard Fmoc-based solid phase synthesis would produce a peptide sequence. An appropriately derivatised VDA could then be conjugated through the N-terminus. Resin cleavage and purification would be as previously described.

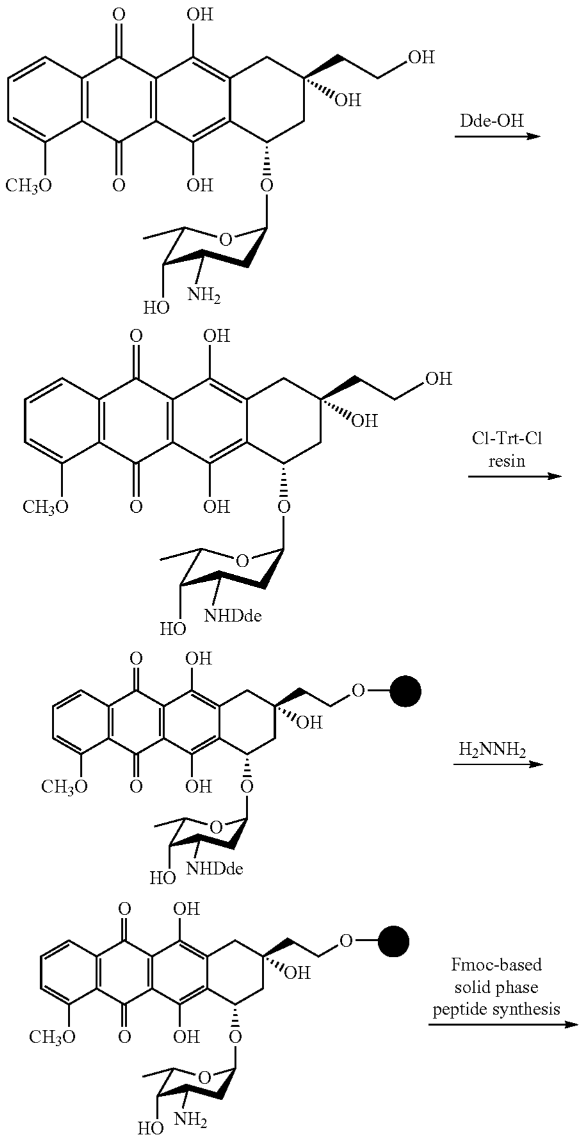

Incorporation of Glycosylated Amino Acids

Amino acids with appropriate side chain functionality (e.g. serine, tyrosine, threonine) can be glycosylated (with mono-, di- or trisaccharides) to produce peptides with enhanced aqueous solubility. Such a carbohydrate-derivatised moiety could be used in place of serine, for example (see scheme below).

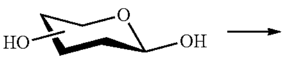

-continued

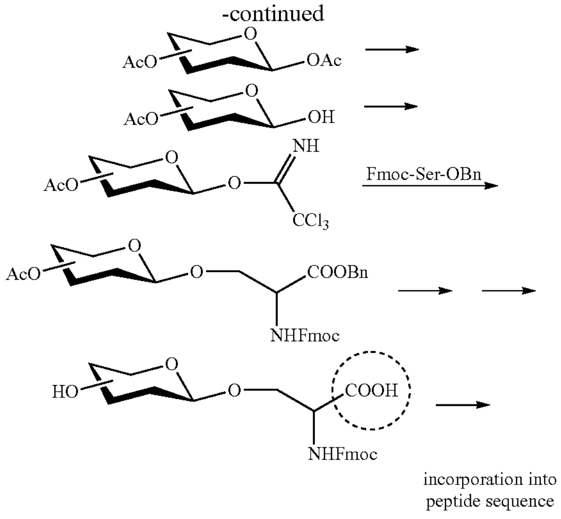

Figure 2:
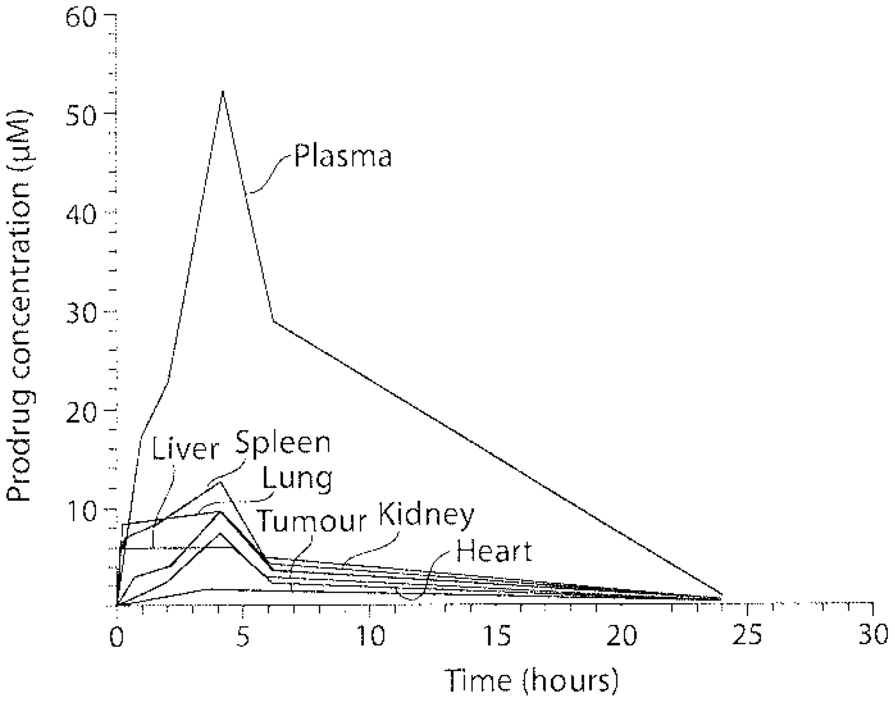
FIG. 2 is a graph showing accumulation and levels of prodrug-1 in tumour-bearing mice following intraperitoneal administration.
Figure 3:
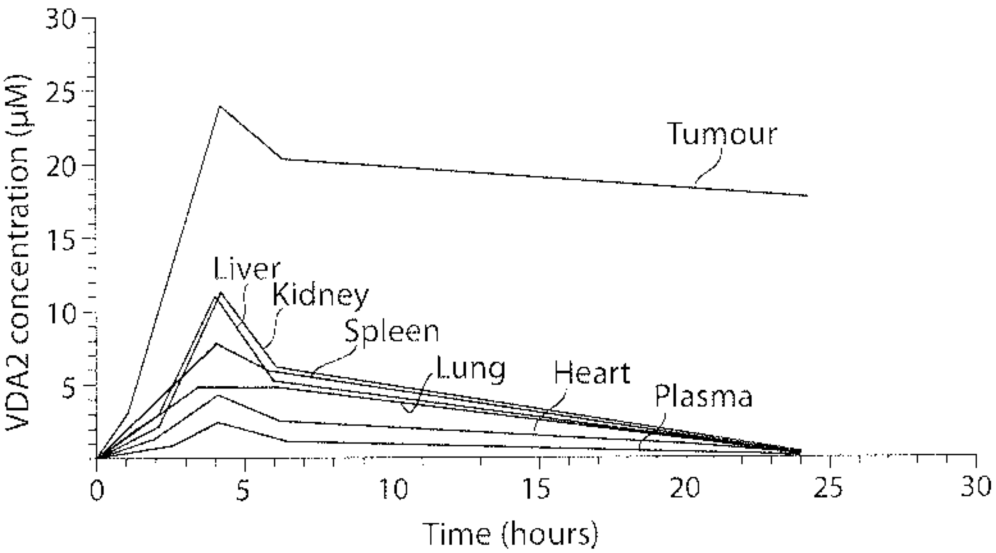
FIG. 3 is a graph demonstrating levels of VDA accumulating following intraperitoneal administration of prodrug-1 to tumour bearing mice.

Results
1) MMP-Activated Prodrug
pan MMP targeted
Structure:

a. Prodrug-1 was stable in plasma and liver, supporting systemic stability of these therapeutics (FIG. 1).

b. Prodrug-1 was metabolised in tumour homogenate, supporting activation of these therapeutics in tumours expressing MMPs (FIG. 1).

b) Prodrug-1 is cleaved rapidly at the Glycine-Homophenylalanine (Gly-Hof) by recombinant MMP-2, MMP-9, MMP-10 and MMP-14 at least. Demonstrated by LC/MS/MS and mass spectrometry (data not shown).

c) Prodrug-1 was administered in vivo via the intraperitoneal route to mice bearing subcutaneous HT1080 tumour model (expression of majority of MMPs). Plasma, tissues and tumours were collected at regular intervals post-dosing. Levels of prodrug and VDA2 were assessed by LC/MS/MS.

a. Prodrug-1 accumulated and was detected in all tissues analysed (FIG. 2).

b. Highest prodrug-1 levels were observed in the tumour (FIG. 2).

c. Prodrug-1 not detectable after 24 hours post-dosing. (FIG. 2).

d. VDA2 was detectable at low levels in normal tissues following prodrug-1 administration (FIG. 3).

(SEQ ID NO: 2)

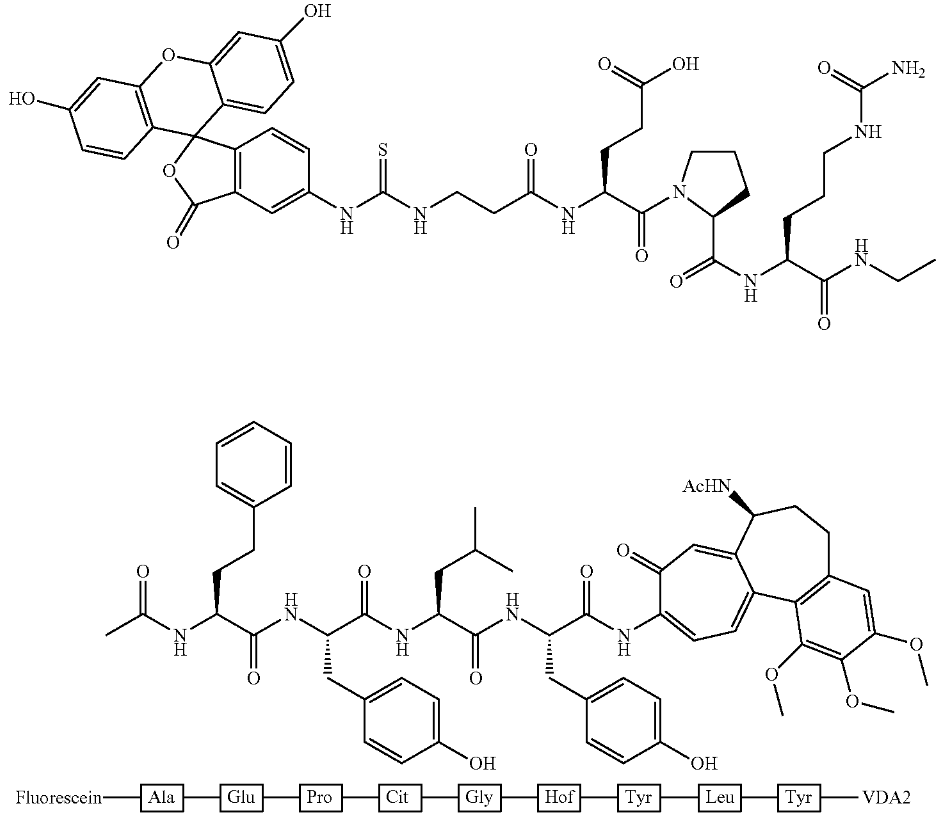

Fluorescein—Ala—Glu—Pro—Cit—Gly—Hof—Tyr—Leu—Tyr—VDA2

(Hof = homophenylalanine; Cit = citrulline; VDA-2 = azademethylcolchicine)

a) Prodrug-1 has been screened using normal mouse plasma, normal mouse liver homogenate and experimental human tumour model homogenate (HT1080 xenograft; known to express majority of MMPs) ex vivo. Prodrug cleavage and metabolism were detected using LC/MS/MS.

e. VDA2 levels were detected at high levels in tumour tissue following prodrug-1 administration (FIG. 3).

f. VDA2 was still detectable at high levels in tumour and was undetectable in normal tissues after 24 hours post-dosing with prodrug-1 (FIG. 3).

2) MMP-Activated Prodrug (ICT-2588)
targeted to Membrane-type MMPs (MT-MMPs)
Structure:

(SEQ ID NO: 3)

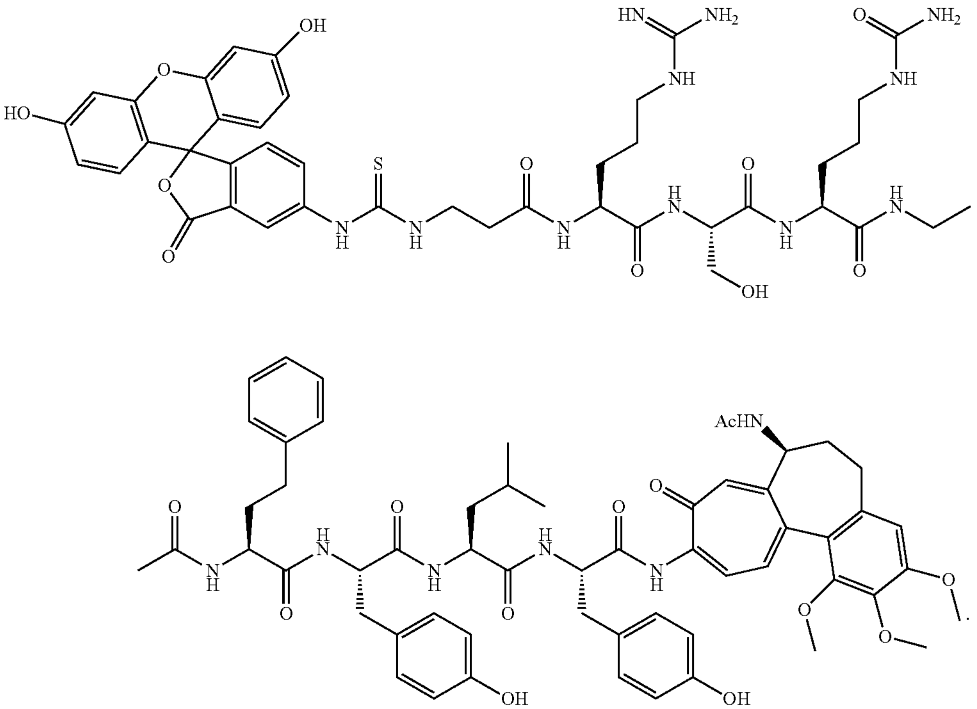

Figure 4:
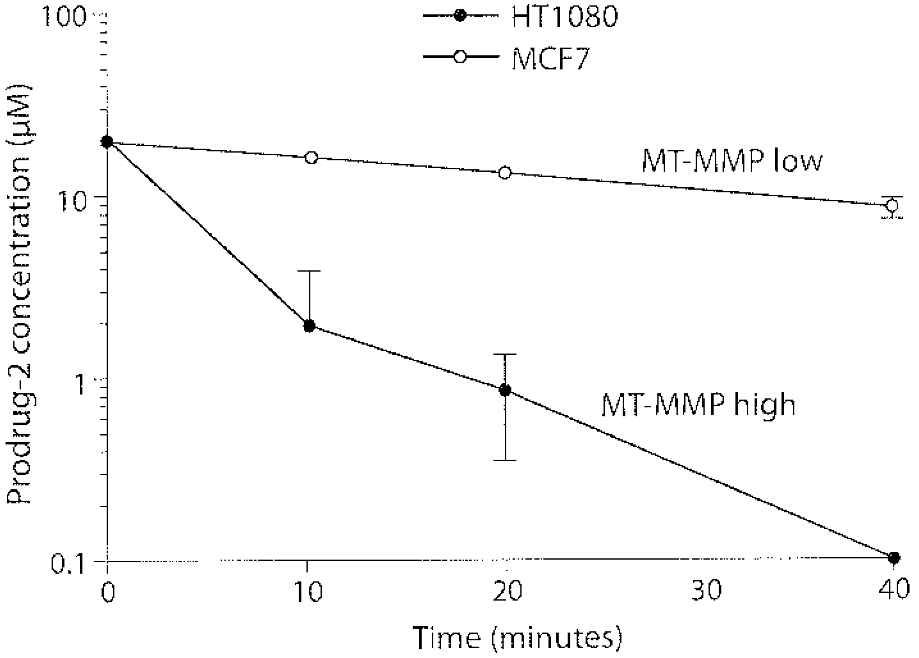
FIG. 4 is a graph showing differential metabolism of prodrug-2 in tumour homogenates expressing high MT1-MMP levels (HT1080) versus tumour homogenates expressing low MT1-MMP levels (MCF-7)
Figure 5:
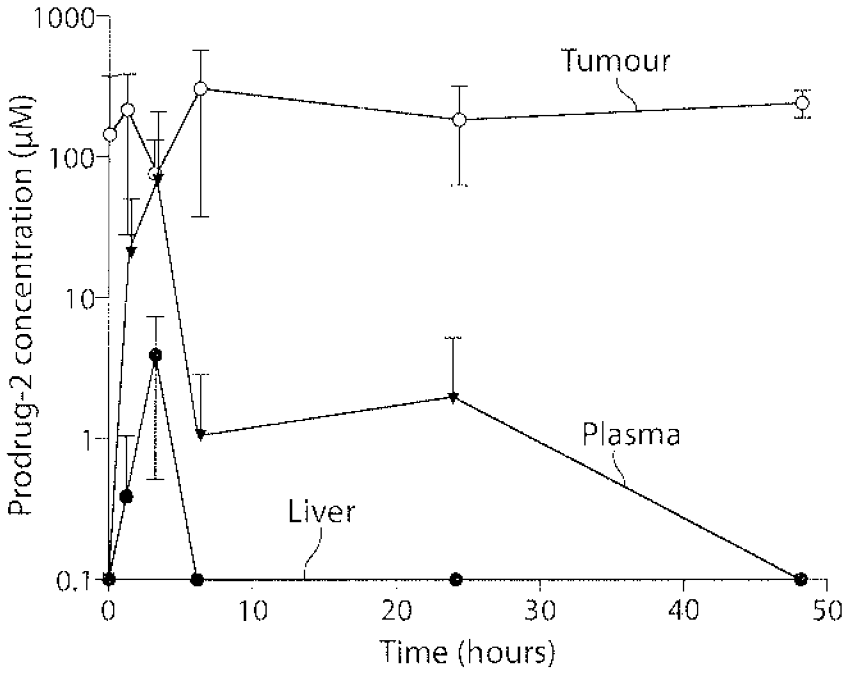
FIG. 5 is a graph showing accumulation and levels of prodrug-2 in HT1080 tumour bearing mice following intraperitoneal administration.
Figure 6:
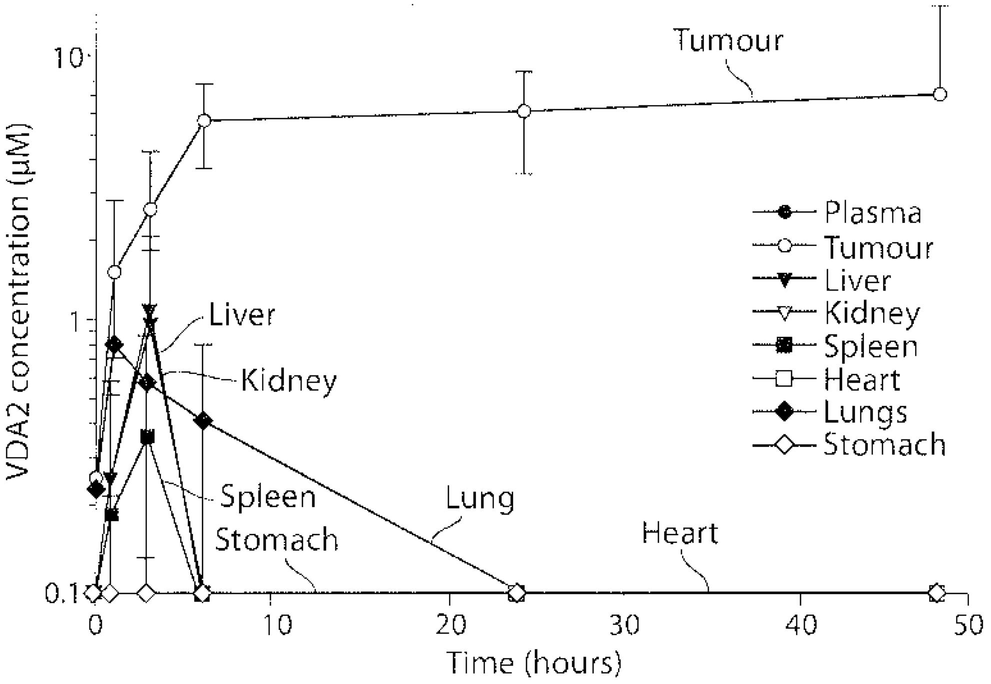
FIG. 6 is a graph demonstrating levels of VDA accumulating following intraperitoneal administration of prodrug-2 to HT1080 tumour bearing mice.

Fluorescein—Ala—Arg—Ser—Cit—Gly—Hof—Tyr—Leu—Tyr—VDA2 d) Compound 1 was modified in order to change the MMP-targeting of the compound from being pan-MMP to MT-MMP selective (Prodrug-2).

a. Arginine was incorporated in place of the Glutamic acid at the P4 position.

b. Proline was removed and replaced with Serine at the P3 position.

e) Prodrug-2 has been screened using normal mouse plasma, normal mouse liver homogenate and experimental human tumour model homogenates demonstrating high MT1-MMP (MMP-14) expression and activity (HT1080) and low MT1-MMP expression and activity (MCF-7) ex vivo. Prodrug-2 cleavage and metabolism were detected using LC/MS/MS.

a. Prodrug-2 remained intact in plasma supporting systemic stability of this therapeutic.

b. Prodrug-2 remained stable in murine liver homogenates.

c. Prodrug-2 was metabolised rapidly in tumour homogenate expressing high MT-MMP levels (HT1080) relative to tumour homogenate expressing low MT-MMP levels (MCF7) (FIG. 4).

d. These data support the systemic stability of this prod rug and the selectivity of activation by MT-MMPs.

f) Prodrug-2 is cleaved differentially by MMPs as shown by LC/MS/MS and mass spectrometry (data not shown):

a. Cleaved rapidly at the Glycine-Homophenylalanine (Gly-Hof) by recombinant MMP-14.

b. Cleaved slowly at the Homophenylalanine-Tyrosine (Hof-Tyr) by recombinant MMP-2. Demonstrating different cleavage to that observed with prodrug-1.

c. Prodrug-2 is not cleaved by recombinant MMP-9, in contrast to prodrug-1.

d. These data support the MMP selective cleavage of prodrug-2.

g) Prodrug-2 was administered in vivo via the intraperitoneal route to mice bearing subcutaneous HT1080 tumour model (MT1-MMP positive). Plasma, tissues and tumours were collected at regular intervals post-dosing. Levels of prodrug-2 and VDA2 were assessed by LC/MS/MS.

a. Prodrug-2 accumulated and was detected in all tissues analysed (FIG. 5).

b. Highest prodrug-2 levels were observed in the tumour (FIG. 5).

c. Liver was representative of all normal tissues analysed (FIG. 5).

d. VDA2 was undetectable in plasma following administration of prodrug-2 (FIG. 6).

e. High concentrations of VDA2 were detected in tumour following prodrug-2 administration (FIG. 6).

f. Levels of VDA2 in tumour were 10 times higher than that detected in normal tissues following administration of prodrug-2 (FIG. 6).

g. High levels of prodrug-2 and VDA2 were still detectable in tumour 48 hours post administration.

3. Synthesised conjugates (based on MT-MMP prodrug) which have proved unsuccessful. Prodrugs including the following endcaps were insufficiently stable in plasma and/or liver (1) 3×D-Serine (2) quinic acid+2×D-Serine (SEQ ID NO: 4)

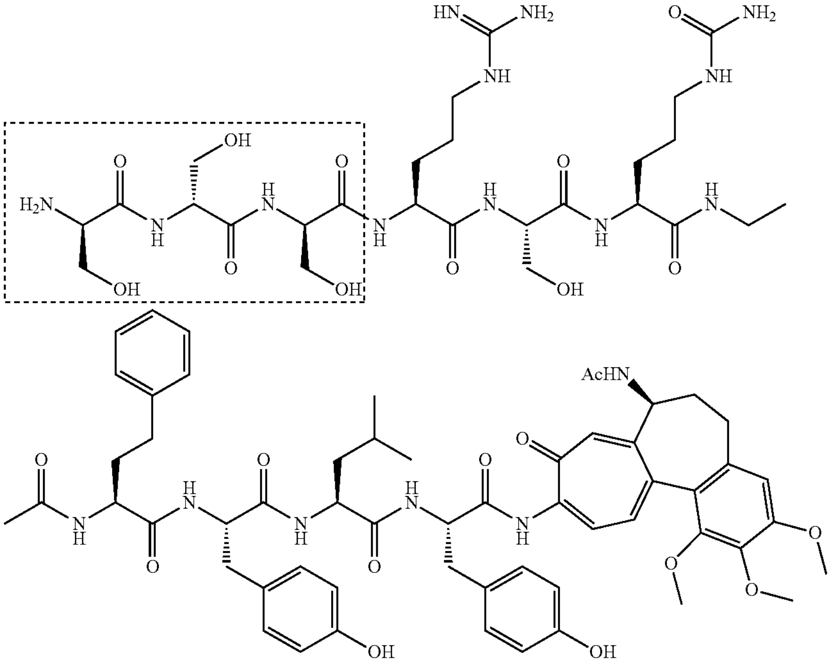

$NH_2$—D-Ser-D-Ser-D-Ser-Arg-Ser-Cit-Gly-HoPhe-Tyr-Leu-Tyr-Warhead (SEQ ID NO: 4)

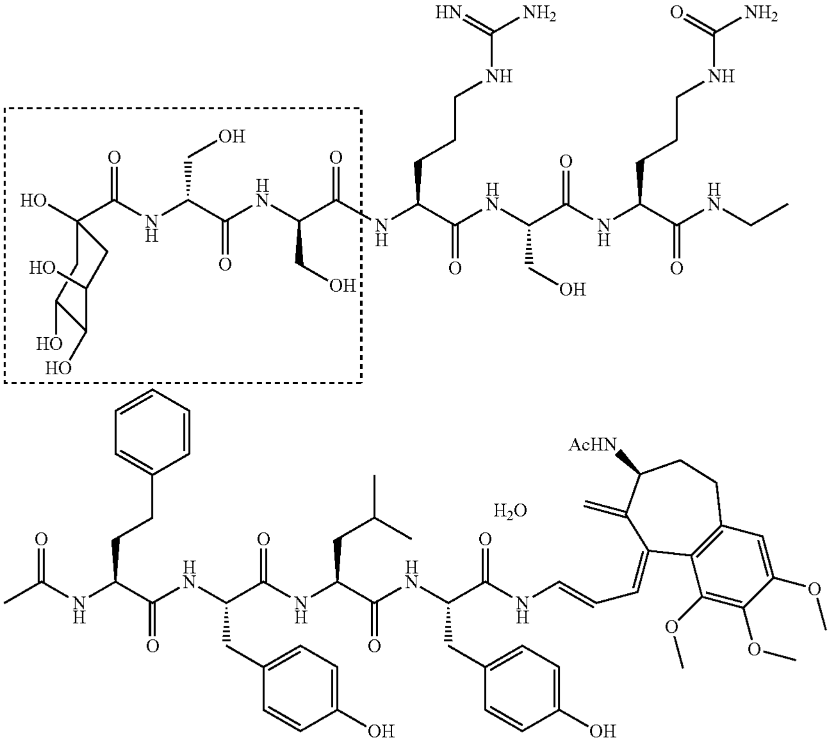

Quinic-D-Ser-D-Ser-Arg-Ser-Cit-Gly-HoPhe-Tyr-Leu-Tyr-Warhead

Example 2

Dose Response Antitumour Study

Materials and Methods

Synthesis of ICT-2588—see Example 1

Synthesis of ICT-2552: Ammonia solution (35%, 15 mL) was added to colchicine (750 mg, 1.88 mmol, 1.00 eq) and the reaction mixture stirred at room temperature overnight. The crude product was washed with KHSO4 (1M, aq), dried with MgSO4, filtered and concentrated under reduced pressure. It was subsequently purified by flash chromatography on silica gel (gradient elution: CH2Cl2/methanol 95:5 to 10:1) to give ICT-2552 as a yellow solid (427 mg, 1.11 mmol, 59%). δH (600 MHz, CDCl3), 7.99 (1H, broad s, NH), 7.56 (1H, d, J 2.1, C8-H), 7.32 (1H, d, J 10.7, 011-H), 6.88 (1H, d, J 11.0, C10-H), 6.52 (1H, s, C4-H), 6.03 (2H, broad s, NH2), 4.68 (1H, ddd, J 12.6, 6.5 and 6.5, C7-H), 3.93 (3H, s, OCH3), 3.88 (3H, s, 00H3), 3.60 (3H, s, OCH3), 2.47 (1H, dd, J 13.4 and 6.2, C5-CH2), 2.35 (1H, ddd, J 13.4, 12.7 and 6.9, C5-CH2), 2.29-2.23 (1H, m, C6-CH2), 1.98 (3H, s, CH3), 1.90-1.88 (1H, m, C6-CH2); ES m/z (%) 385 [M+1-1]+(100).

ICT-2552 and ICT-2588 ('prodrug') were administered as a single dose via the intraperitoneal route to Balb/C mice bearing subcutaneous HT1080 xenografts. Each of the nine dosing groups comprised 8 mice. The anti-tumour effects of the compounds were assessed by determination of tumour volume and the existence of off-target toxicity was ascertained via monitoring mouse body weight.

The dosing groups evaluated ICT-2588 (prodrug) relative to the molar equivalent dose of ICT-2552 (warhead), and were:

10% DMSO/oil (solvent control)

ICT-2588 at 37.5 mg/kg; 50.0 mg/kg; 62.5 mg/kg; 75.0 mg/kg

ICT-2552 at 7.5 mg/kg; 10.0 mg/kg; 12.5 mg/kg; 15 mg/kg

Results

Figure 7:
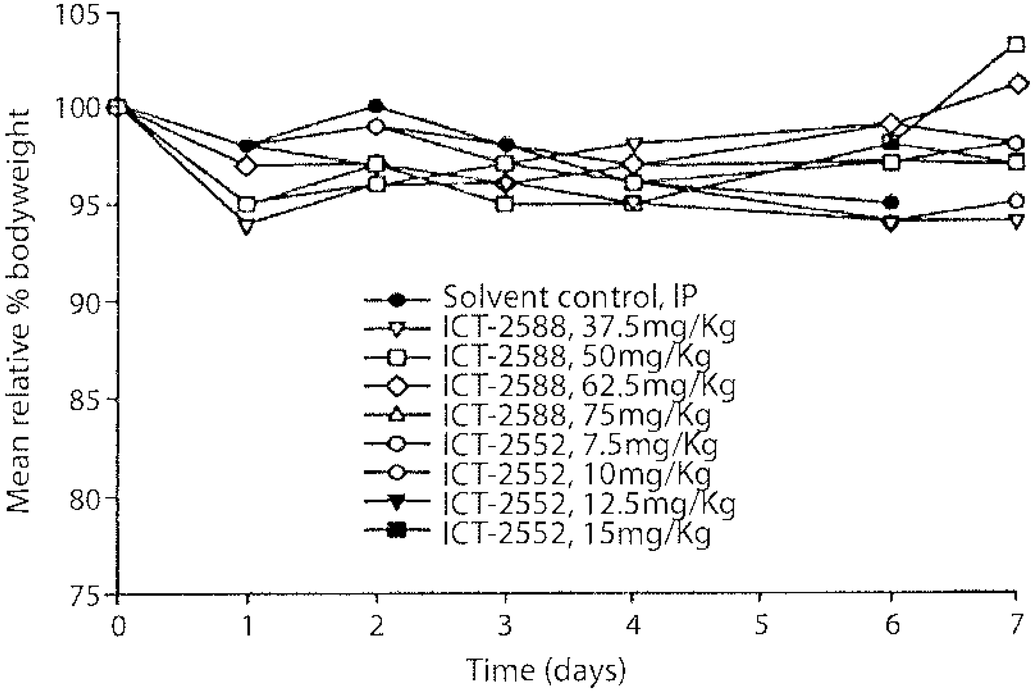
FIG. 7: Relative mouse bodyweights during dose escalation study.

No significant loss in body weight was observed throughout the study (FIG. 7)

The weight of all mice was within the tolerated loss of 15% of bodyweight, therefore the compounds are not classified as toxic to the whole body system.

Example 3

Tumour Response Study

Results

Figure 8:
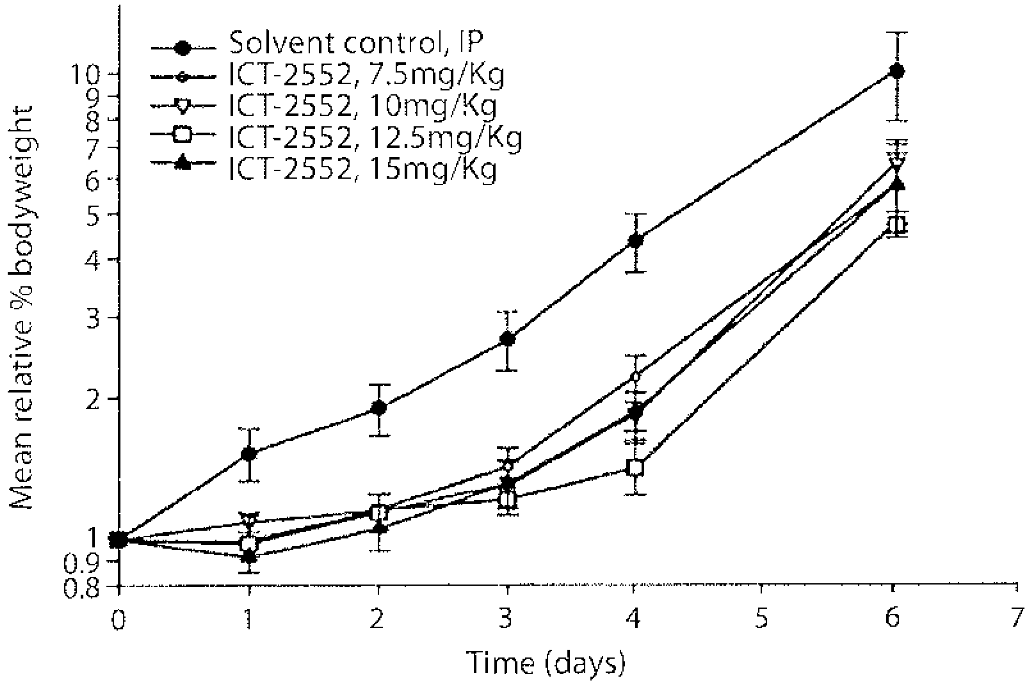
FIG. 8: Tumour growth during treatment with ICT-2522 (warhead)
Figure 9:
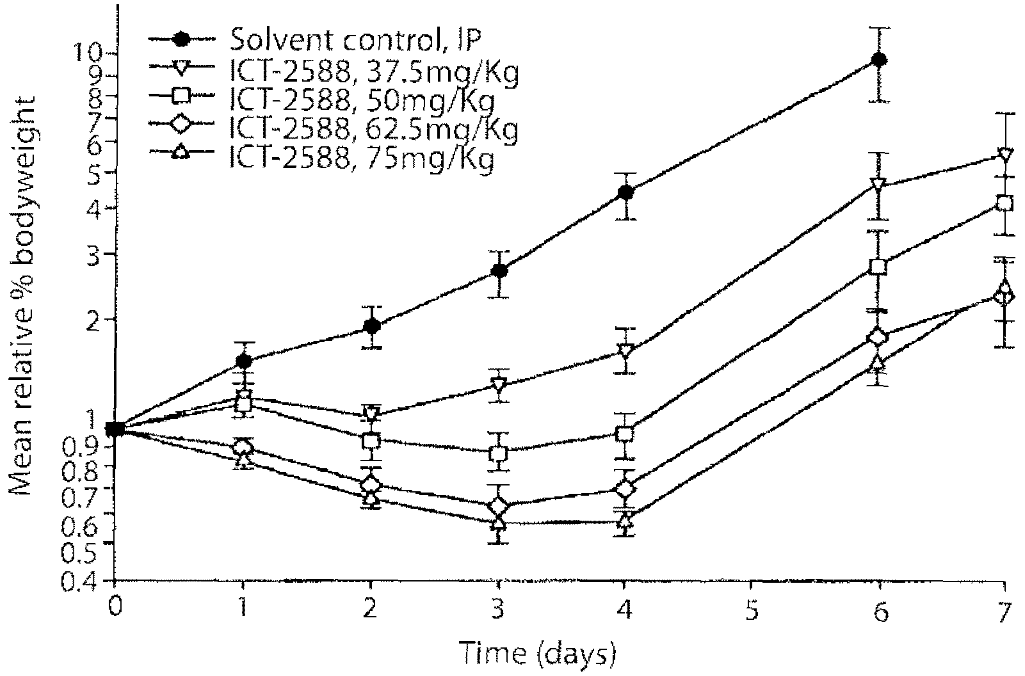
FIG. 9: Tumour growth during treatment with ICT-2588 (prodrug)
Figure 10A:
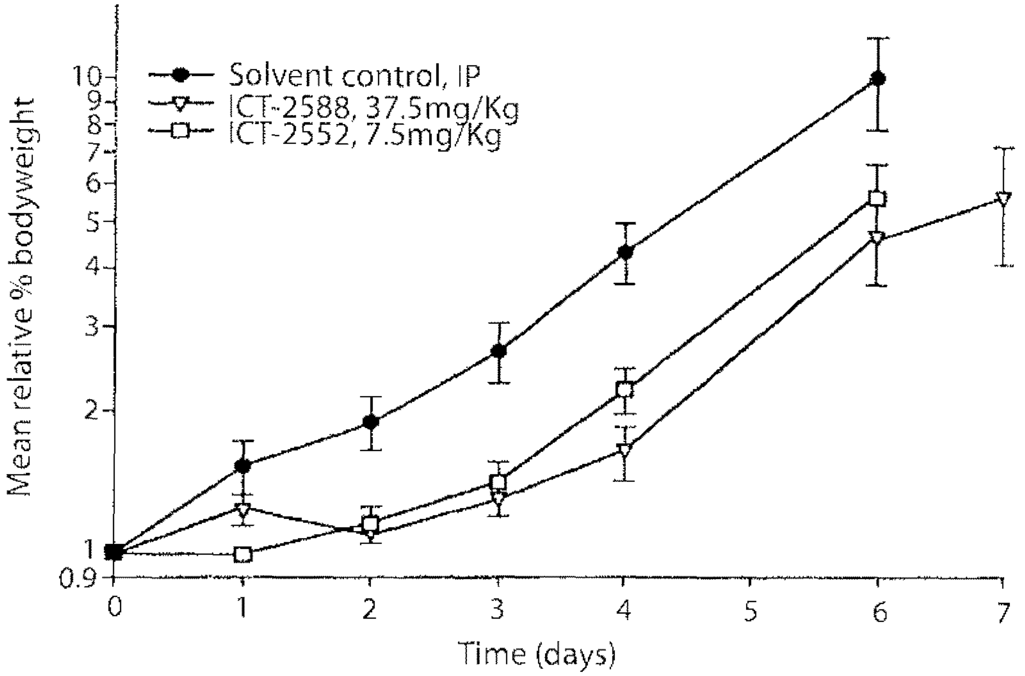
FIG. 10A-FIG. 10D Tumour growth curves for mice treated with pro-drug (ICT-2588) compared with warhead (ICT-2552) administered at the molar equivalent dose.
Figure 10B:
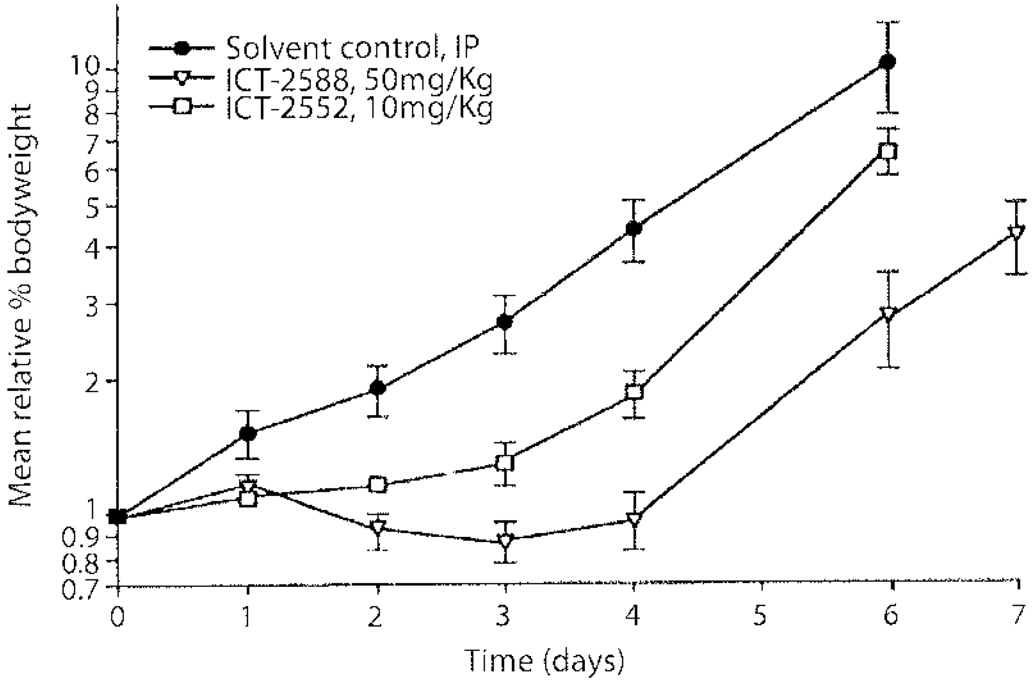
Figure 10C:
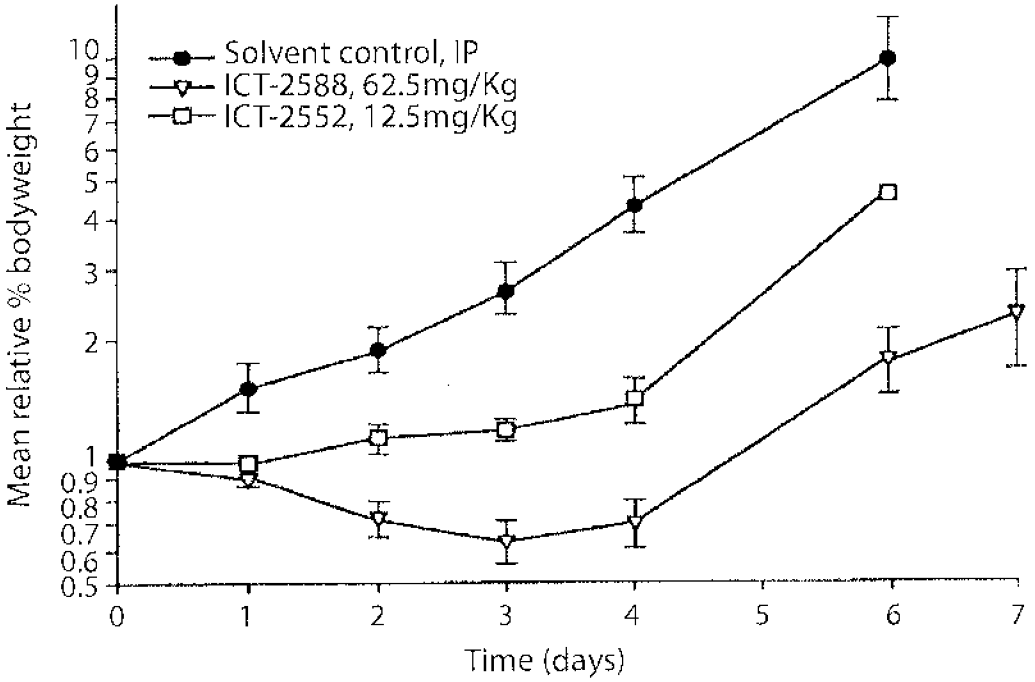
Figure 10D:
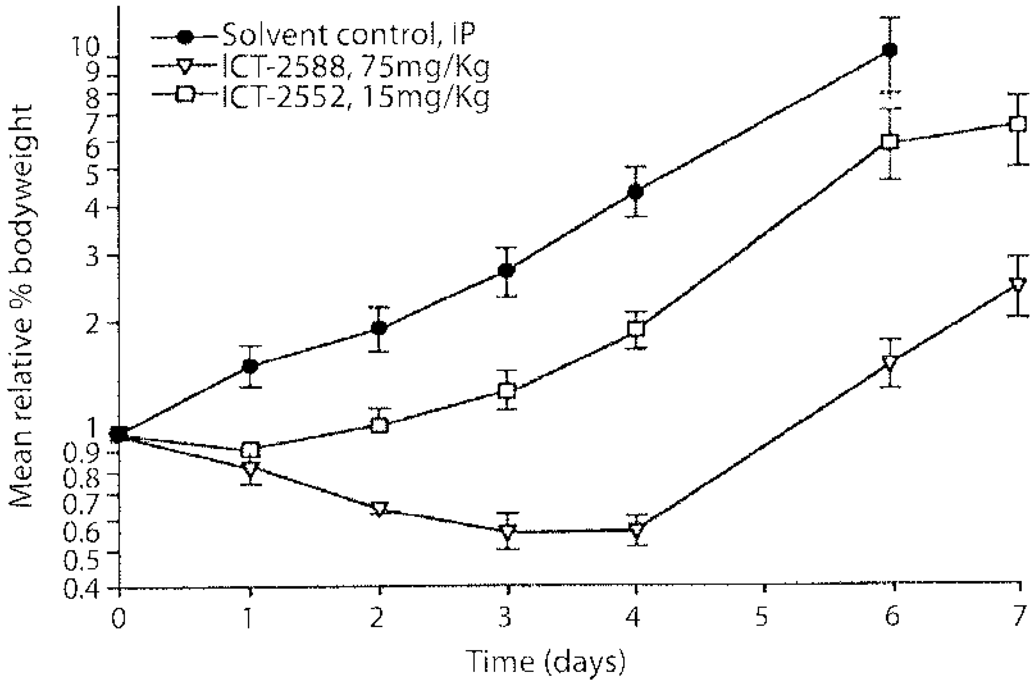

The results of the study are shown in FIGS. 8 to 10 and in the following Tables. Tumour responses were observed at all tested dose levels of ICT-2522 and ICT-2588.

TABLE 1

Antitumour efficacy of compounds relative to untreated control group

| Compound | Dose (mg/kg) | Mean time to RTV2 (days) | Median time RTV2 (days) | Growth delay (days) | Significance [a] | Maximum % weight loss (day)[b] |
|---|---|---|---|---|---|---|
| Control | — | 2.3 | 2.2 | — | — | 5 (6) |
| ICT-2588 | 37.5 | 4.4 | 4.2 | 2.0 | $p < 0.01$ | 3 (3) |
| ICT-2588 | 50.0 | 5.5 | 6.0 | 3.8 | $p < 0.01$ | 5 (3) |
| ICT-2588 | 62.5[c] | 7.7 | 7.8 | 5.6 | $p < 0.01$ | 4 (3) |
| ICT-2588 | 75.0 | 6.8 | 6.6 | 4.4 | $p < 0.01$ | 5 (3) |
| ICT-2552 | 7.5 | 4.0 | 3.8 | 1.6 | $p < 0.01$ | 3 (4) |
| ICT-2552 | 10.0 | 4.4 | 4.2 | 2.0 | $p < 0.01$ | 6 (6) |
| ICT-2552 | 12.5 | 4.5 | 4.7 | 2.5 | $p < 0.01$ | 6 (1) |
| ICT-2552 | 15.0 | 4.1 | 4.1 | 1.9 | $p < 0.01$ | 5 (1) |

[a] Statistics worked out based on the time it takes the tumour to double in size from day 0.

[b]Maximum weight loss well within the accepted levels of 15%.

[c]One animal showed complete tumour remission (final measurement day 21)

A significant delay in tumour growth was observed at all evaluated doses of ICT-2552 (warhead) and ICT-2588 (prodrug).

A relationship between dose of compound and degree of tumour growth delay was observed with both compounds. The effects being greater with ICT-2588 (prodrug)

One animal demonstrated complete tumour remission with ICT-2588 at a dose of 62.5 mg/kg

TABLE 2

Comparison of antitumour efficacy between dose of ICT-2588 (prodrug) and ICT-2552 (warhead) administered at the molar equivalent dose

| Dose of ICT-2588 (mg/kg) | Dose of ICT-2552 (mg/kg) | Growth delay with prodrug (Days) | Growth delay with warhead (Days) | Significance of differential between equimolar doses of ICT-2588 and ICT-2552[a] |
|---|---|---|---|---|
| 37.5 | 7.5 | 2.0 | 1.6 | $p > 0.05$ |
| 50.0 | 10.0 | 3.8 | 2.0 | $p < 0.05$ |
| 62.5[c] | 12.5 | 5.6 | 2.5 | $p < 0.05$ |
| 75.0 | 15.0 | 4.4 | 1.9 | $p < 0.01$ |

[a]Statistics worked out based on the time it takes the tumour to double in size from day 0.

[c]One animal showed complete tumour remission (final measurement day 21)

ICT-2588 (prodrug) induced a significantly greater antitumour response than ICT-2522 (warhead) when administered at equimolar doses

Example 4

Figure 11:
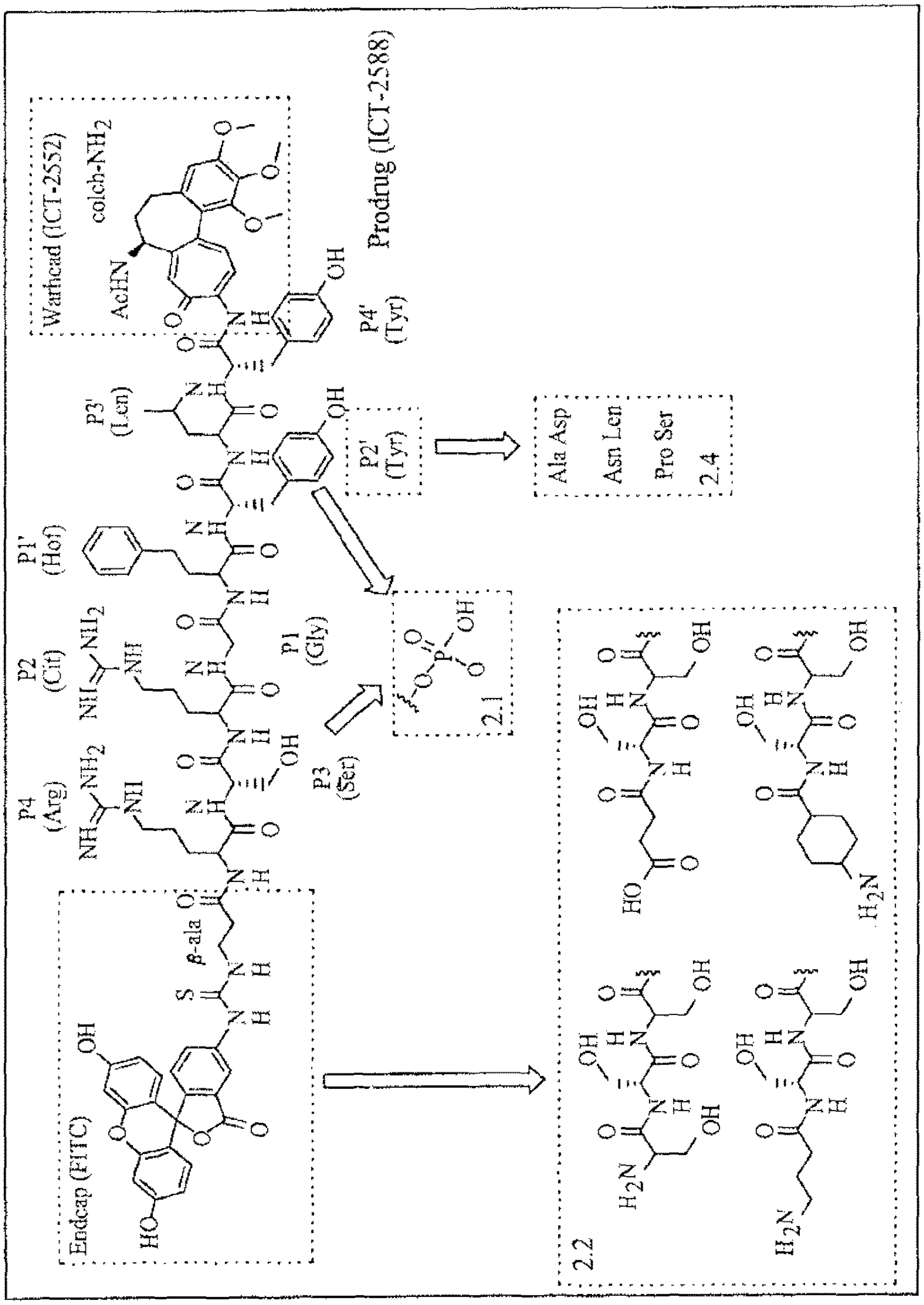
FIG. 11 Pro-drug, ICT-2588, showing modifications including phosphorylated amino acid residues, end-cap, warhead and P2' alternatives.
Figure 12:
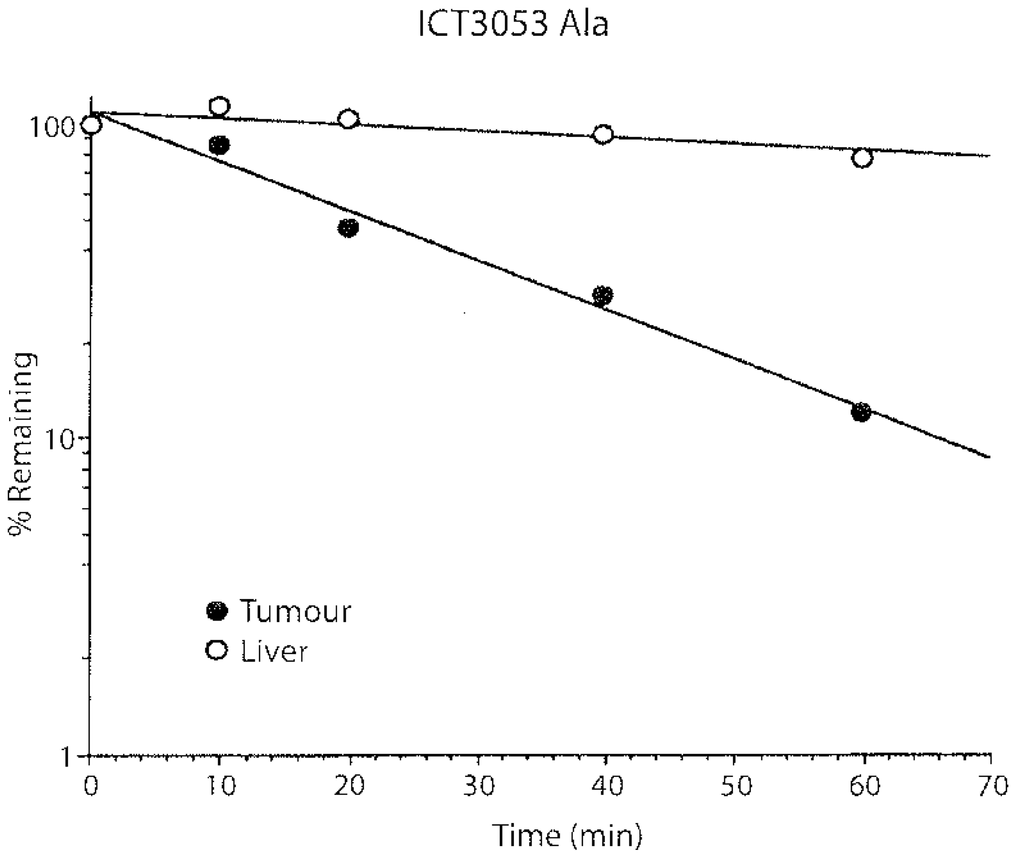
FIG. 12 A graph demonstrating the stability of ICT 3053 (P2'=Ala) in both tumour (HT1080) and liver (murine) homogenates. This is an example of the data obtained for this series of molecules and a summary of the data is given in table 1.
Figure 13A:
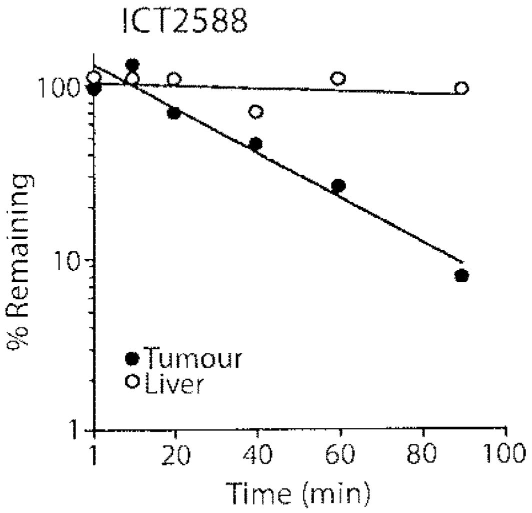
FIG. 13A-FIG. 13D Stability data for prodrug (ICT2588) (FIG. 13A) molecules with phosphate attached to serine (ICT3047) (FIG. 13B) tyrosine (ICT 3048) (FIG. 13D) and both serine and tyrosine (ICT3028) (FIG. 13C). Data show percent of parent molecule remaining following incubations in tumour (HT1080, closed symbols) and murine liver (open symbols) homogenate for the indicated time. This is representative data from multiple experiments. Chromatographic separations were established to monitor the dephosphorylation of each molecule.
Figure 13B:
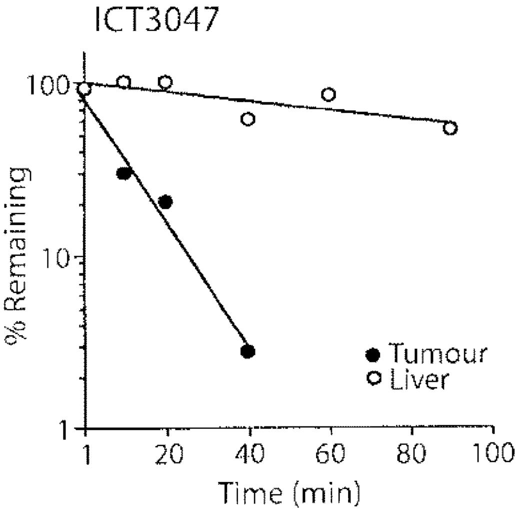
Figure 13C:
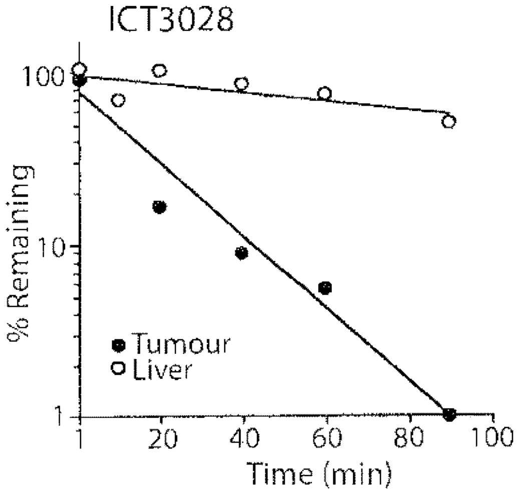
Figure 13D:
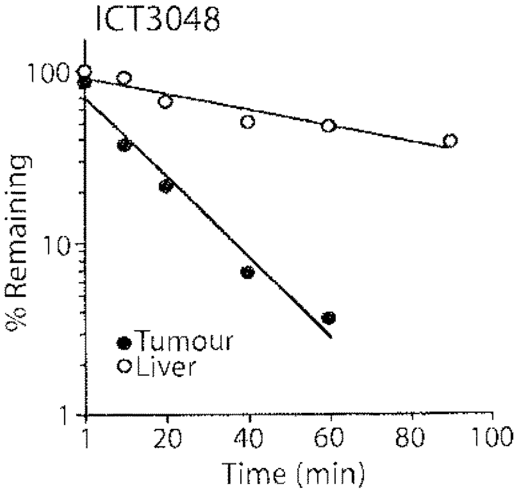

Modifications to ICT-2588 i) Improvement of Prodrug Solubility Through Introduction of Phosphorylated Amino Acid Side Chains To increase prodrug solubility, phosphorylated amino acid side are introduced chains into the peptide sequence of ICT-2588 (hydrolysable by plasma phosphatases). Phosphate-derivatised amino acids are commercially available, as benzyl-protected moieties, and are incorporated into peptides using our synthetic methodology. We are synthesising and evaluating phosphorylation modification of two sites within the peptide sequence; P2' (Tyr), P3 (Ser), and both P2' and P3 (see FIG. 11). In addition, we are addressing the effect of phosphorylation of P2' (Tyr) upon prodrug activation by MT-MMPs (cleave at P1-P1') and MMP-2 (cleave at P1'-P2') to address the potential for further increasing MMP selectivity.

ii) Improvement of Solubility Via Modification of Prodrug Endcapping Group

We are exploring the replacement of the fluorescein group with a more hydrophillic group (see FIG. 11) as alternative prodrugs with improved solubility. Our objective is to improve prodrug solubility whilst retaining MT-MMP selectivity, tumour selective activation and antitumour activity. Prodrugs incorporating these alternative endcaps to ICT2588 are being assessed in terms of compound solubility relative to parent prodrug in vitro, prodrug stability and activation in the HT1080 tumour model, mouse plasma and liver homogenate ex vivo, and retention and potential improvement of MT-MMP selectivity.

iii) Modification of P2' Site within Prodrug

The effects of modification of the P2' site (Tyr) of the prodrug with reference to tissue stability, tumour cleavage and MMP activation ex vivo are being assessed. The focus is on the P2' site of the prodrug as we have demonstrated cleavage by other non-MT-MMPs at both the P1'-P2' and P2'-P3' sites. We are using prodrug variants incorporating the main types of amino acid side chain (Ala, Asp, Asn, Leu, Ser, Pro).

iv) Development of Dual-Headed Prodrug Incorporating Doxorubicin

Following treatment with ICT2588 a thin viable rim of tumour cells was observed at the tumour periphery. Current understanding of tumour vascularisation indicates that the viable rim is maintained by the vasculature of the immediately surrounding normal tissues. A consequence of this is that administration of a VDA-releasing prodrug in combination with standard chemotherapy should increase further the antitumour effect observed. We are developing a dual-headed prodrug containing our azademethylcolchicine warhead (ICT2552) and a doxorubicin warhead (replacing the endcap) (see below). We are evaluating this dual-headed prodrug in terms of prodrug stability and activation in the HT1080 tumour model, mouse plasma and liver homogenate ex vivo.

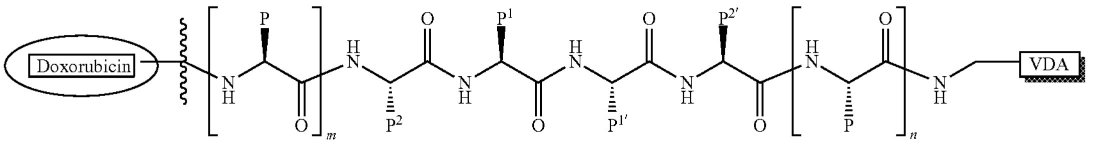

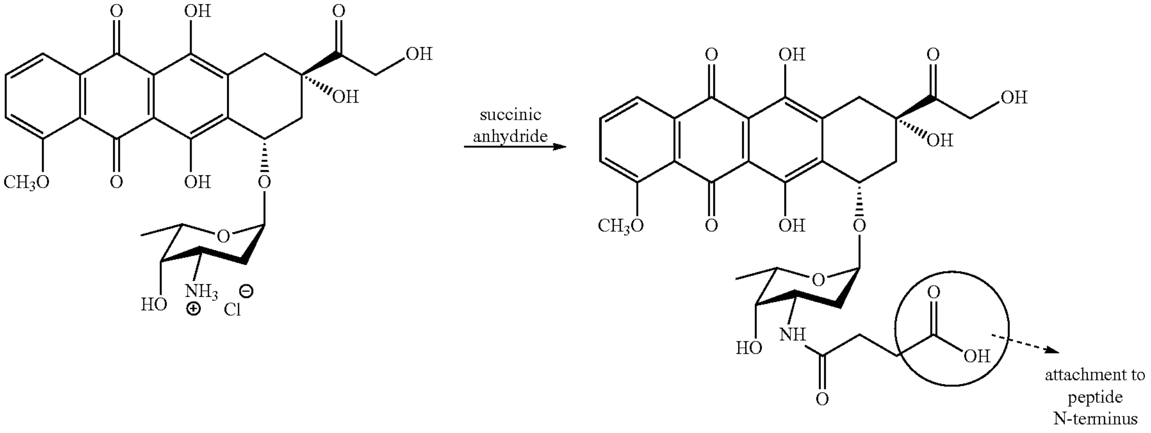

Derivatisation at the amine is required since attachment to the peptide will be through the N-terminus. Current strategy is to acylate with succinic anhydride, yielding a succinate derivative bearing a free carboxylic acid which can be linked to the peptide via an amide bond. Alternative strategy to be evaluated is to use the side chain of aspartic acid with alkyl/aryl blocking group R.

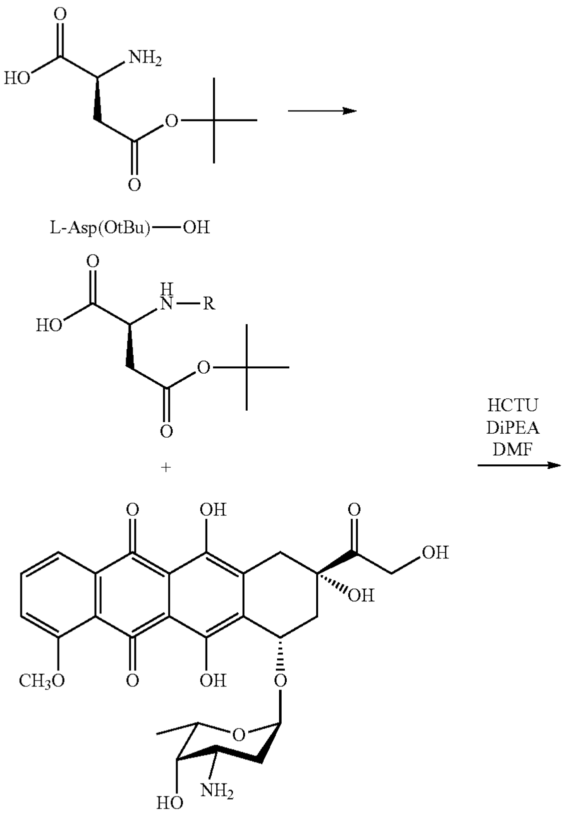

-continued

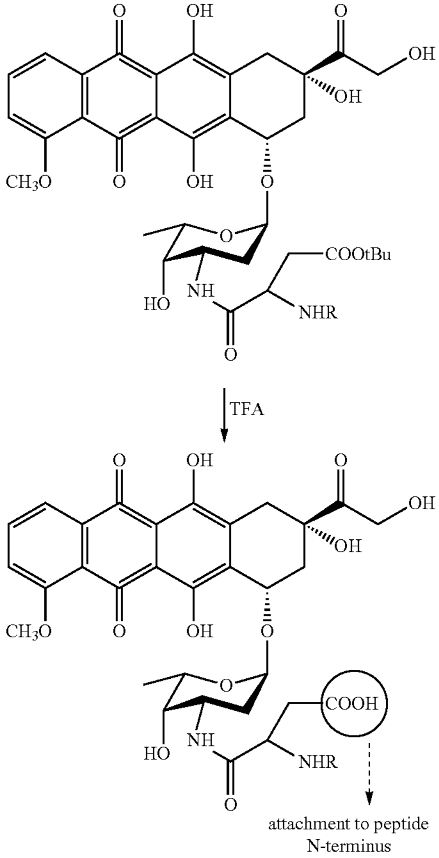

Table 3 is a summary of stability data for a series of molecules with changes in the P2' position. Half lives are the mean taken from four independent experiments. Liver represent murine liver homogenate and tumour represents HT1080.

| | P2' AA | Liver t½ (min) | Tumour t½ (min) |
|---|---|---|---|
| ICT2588 | Tyr | 149 | 33 |
| ICT3055 | Asp | 67 | 7 |
| ICT3053 | Ala | 76 | 17 |
| ICT3054 | Ser | 66 | 9 |
| ICT3078 | Asn | 76 | 11 |

-continued

| | P2' AA | Liver t½ (min) | Tumour t½ (min) |
|---|---|---|---|
| ICT3097 | Pro | 110 | 24 |
| ICT3080 | Leu | 134 | 48 |

What is claimed:

1. A method of treating a solid tumor in a subject comprising administering an effective amount of a compound, or pharmaceutically acceptable salt thereof, comprising a vascular disrupting agent (VDA) associated with a matrix metalloproteinase (MMP) proteolytic cleavage site, wherein the VDA is selected from the group consisting of azademethylcolchicine, colchicine, azacolchicine, N-methyl desacetylcolchicine, desacetylcolchicine, N-acetylcolchinol-O-phosphate, colchicinoids, combrestatins, phenstatin, podophyllotoxins, steganacins, amphethinile, stilbenes, flavonoids, vincristine, vinblastine, vinflunine, maytansinoids, phomopson A, rhizoxin, auristatin, and dolstatin, and the MMP proteolytic cleavage site comprises the amino acid sequence -Leu-P2'-Hof-Gly-Cit-Ser-Arg-, wherein P2' is an amino acid selected from Asp, Ala, Ser, Asn, Pro, Leu, Arg and Thr.

2. The method according to claim 1, wherein the VDA is selected from the group consisting of azademethylcolchicine, colchicine, azacolchicine, N-methyl desacetylcolchicine, and desacetylcolchicine.

3. The method of claim 2, wherein the VDA is azademethylcolchicine.

4. The method according to claim 1, wherein the compound further comprises a capping group c on the N- or C-terminus of the peptide which prevents non-specific degradation of the peptide by enzymes other than MMPs.

5. The method of claim 1, wherein the amino acid at P2' is methylated.

6. The method of claim 1, wherein an anti-cancer agent is further linked to the peptide comprising the MMP proteolytic cleavage site.

7. The method of claim 6, wherein the anti-cancer agent is selected from the group consisting of 5-fluorouracil, anthracycline, doxorubicin, vinca alkaloid, taxane, a cytotoxic nucleotide, a biotoxin, radiotherapeutic, hormonal agent, colchicine, azademethylcolchicine, N-methyl desacetylcolchicine and desacetylcolchicine.

8. The method of claim 7, wherein the anti-cancer agent is doxorubicin.

9. The method of claim 1, wherein the compound is in the form of a pharmaceutical formulation comprising the compound and at least one additional pharmaceutically acceptable excipient, diluent or carrier.

10. The method of claim 9, wherein the pharmaceutical formulation further comprises a second therapeutic agent selected from the group consisting of cisplatin, carboplatin, cyclophosphamide, melphalan, carmustine, methotrexate, 5-fluorouracil, cytarabine, mercatopurine, daunorubicin, doxorubicin, epirubicin, vinblastine, vincristine, dactinomycin, mitomycin C, taxol, L-asparaginase, granulocyte colony stimulating factor (G-CSF), etoposide, colchicine, deferoxamine mesylate and camptothecin.

11. The method of claim 1, wherein the compound is of formula (I)

X—Y (I), wherein X is the VDA; and

Y is the peptide comprising the MMP proteolytic cleavage site.

12. The method of claim 11, wherein Y is a peptide sequence of between seven and ten amino acids.

13. The method of claim 1, wherein the compound is of formula (II)

X—Y-*c* (II), wherein X is the VDA;

Y is the peptide comprising the MMP proteolytic cleavage site; and c is a capping group which prevents non-specific degradation of the peptide by enzymes other than MMPs.

14. The method of claim 13, wherein c is selected from the group consisting of fluorescein isothiocyanate and fluorescein.

15. The method of claim 13, wherein c is the formula $(c)_n$ and wherein n is an integer between 1 and 5.

16. The method of claim 15, wherein c is a non-natural amino acid and n is 3.

17. The method of claim 1, wherein the compound is of formula (III)

X-*a*-Y (III), wherein X is the VDA;

Y is the peptide comprising the MMP proteolytic cleavage site; and a is a linker directly or indirectly associated with X and wherein the linker is a single amino acid or amino acid sequence.

18. The method of claim 1, wherein the compound is of formula (IV)

X-*a*-Y-*c* (IV), wherein X is the VDA;

Y is the peptide comprising the MMP proteolytic cleavage site;

a is a linker directly or indirectly associated with X and wherein the linker is a single amino acid or amino acid sequence; and c is a capping group which prevents non-specific degradation of the peptide by enzymes other than MMPs.

19. The method of claim 1, wherein the compound is of formula (V)

X—Y-*b*-*c* (V), wherein X is the VDA;

Y is the peptide comprising the MMP proteolytic cleavage site;

b is a spacer group directly or indirectly linked to Y and wherein the spacer is selected from the group consisting of a single amino acid, amino acid sequence and a succinyl group; and c is a capping group which prevents non-specific degradation of the peptide by enzymes other than MMPs.

20. The method of claim 1, wherein the compound is of formula (VI)

X-*a*-Y-*b*-*c* (VI), wherein X is the VDA;

Y is the peptide comprising the MMP proteolytic cleavage site;

a is a linker directly or indirectly associated with X and wherein the linker is a single amino acid or amino acid sequence;

b is a spacer group directly or indirectly linked to Y and wherein the spacer is selected from the group consisting of a single amino acid, amino acid sequence and a succinyl group; and c is a capping group which prevents non-specific degradation of the peptide by enzymes other than MMPs.

21. The method of claim 1, wherein the compound is of formula (VII)

X—Y—Z (VII), wherein X is the VDA;

Y is the peptide comprising the MMP proteolytic cleavage site; and

Z is an anti-cancer agent selected from the group consisting of a VDA, an antimetabolite and a cytotoxic agent, wherein the VDA is selected from the group consisting of azademethylcolchicine, colchicine, azacolchicine, N-methyl desacetylcolchicine, desacetylcolchicine, N-acetylcolchinol-O phosphate, colchicinoids, combrestatins, phenstatin, podophyllotoxins, steganacins, amphethinile, stilbenes, flavonoids, vincristine, vinblastine, vinflunine, maytansinoids, phomopson A, rhizoxin, auristatin, and dolstatin, the antimetabolite is 5-fluorouracil, and the cytotoxic agent is selected from the group consisting of anthracycline and doxorubicin.

22. The method of claim 21, wherein Z is doxorubicin.

23. The method of claim 21, wherein X is selected from azademethylcolchicine, colchicine, azacolchicine, N-methyl desacetylcolchicine, and desacetylcolchicine.

24. The method of claim 21, wherein X and Z are each independently selected from azademethylcolchicine, colchicine, azacolchicine, N-methyl desacetylcolchicine, and desacetylcolchicine.

25. The method of claim 1, wherein the method further comprises administering a second therapeutic agent.

26. The method of claim 25, wherein the second therapeutic agent is selected from the group consisting of cisplatin, carboplatin, cyclophosphamide, melphalan, carmustine, methotrexate, 5-fluorouracil, cytarabine, mercaptopurine, daunorubicin, doxorubicin, epirubicin, vinblastine, vincristine, dactinomycin, mitomycin C, taxol, L-asparaginase, G-CSF, etoposide, colchicine, deferoxamine mesylate and camptothecin.

27. The method of claim 1, wherein the solid tumor is selected from the group consisting of a tumor of the prostate, breast, head and neck, mouth, oral cavity, nose, trachea, lung, tongue, esophagus, stomach, small intestines, colon, liver, pancreas, gall bladder, rectum, thyroid, pituitary, adrenal glands, urinary bladder, kidney, ovary, uterus, cervix, penis, scrotum, testes, skin, brain, spinal cord, glial cells, neurons, lymphoid system, bone, cartilage, adipose tissue, smooth muscle, skeletal muscle, nerve sheath, blood vessels, mesothelium and gastrointestinal stroma.

28. The method of claim 27, wherein the solid tumor is a non-small cell lung carcinoma.

* * * * *